(12) United States Patent
Nakayama et al.

(10) Patent No.: US 7,345,179 B2
(45) Date of Patent: Mar. 18, 2008

(54) PROCESS FOR PRODUCING PYRROLIDINE DERIVATIVE

(75) Inventors: Atsushi Nakayama, Tokyo (JP); Nobuo Machinaga, Tokyo (JP); Yoshiyuki Yoneda, Tokyo (JP); Masaki Setoguchi, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 143 days.

(21) Appl. No.: 10/556,043

(22) PCT Filed: May 7, 2004

(86) PCT No.: PCT/JP2004/006471

§ 371 (c)(1),
(2), (4) Date: Nov. 8, 2005

(87) PCT Pub. No.: WO2004/099136

PCT Pub. Date: Nov. 18, 2004

(65) Prior Publication Data

US 2007/0105935 A1    May 10, 2007

(30) Foreign Application Priority Data

May 9, 2003 (JP) .............................. 2003-131978
May 22, 2003 (JP) .............................. 2003-144430
Aug. 29, 2003 (JP) .............................. 2003-209579

(51) Int. Cl.
*C07F 9/02* (2006.01)
(52) U.S. Cl. ..................................... 548/414
(58) Field of Classification Search ................. 548/414
See application file for complete search history.

(56) References Cited

U.S. PATENT DOCUMENTS 7,157,487 B2 * 1/2007 Nakayama et al. ......... 514/415

FOREIGN PATENT DOCUMENTS

| JP | 61-251635 | 11/1986 |
| JP | 06-306025 | 11/1994 |
| WO | 2001/00206 | 1/2001 |
| WO | 02/053534 | 7/2002 |

OTHER PUBLICATIONS

U.S. Appl. No. 10/584,240, filed Jun. 26, 2006, Nakayama et al.
U.S. Appl. No. 10/556,043, file Nov. 8, 2005, Nakayama et al.
U.S. Appl. No. 10/584,141, filed Jun. 26, 2006, Takayanagi et al.

* cited by examiner

*Primary Examiner*—Kamal A. Saeed
*Assistant Examiner*—Robert Havlin
(74) *Attorney, Agent, or Firm*—Oblon, Spivak, McClelland, Maier & Neustadt, P.C.

(57) ABSTRACT

This invention provides an industrially useful process for producing 1,4-transcyclohexanecarboxylic acid derivative (1) which has excellent VLA-4 inhibitory action and safety, and an intermediate which is useful in such method. More particularly, this invention relates to a process for converting a compound of formula (I) into a compound of formula (VI) by the reaction scheme:

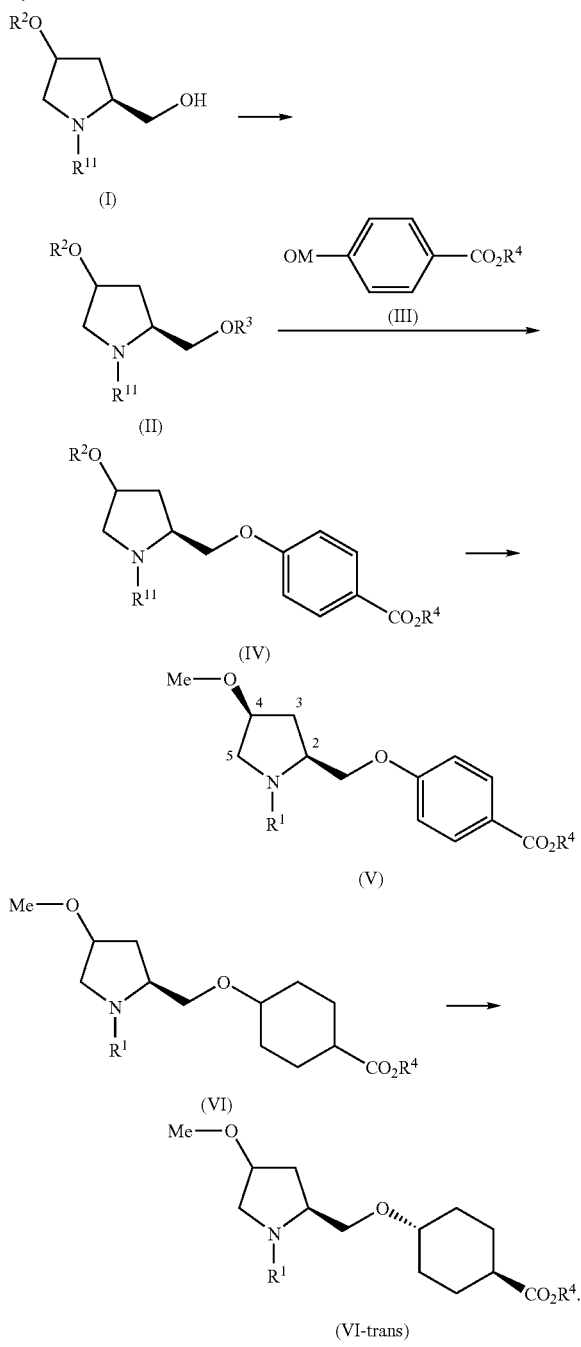

12 Claims, No Drawings

PROCESS FOR PRODUCING PYRROLIDINE DERIVATIVE

TECHNICAL FIELD

This invention relates to a process for producing a compound which is useful as an intermediate in producing a compound exhibiting excellent VLA-4 inhibitory action and high safety. This invention also relates to such a novel and useful intermediate.

BACKGROUND ART

The compound represented by the following general formula (1) is expected to be a highly safe pharmaceutical compound having an anti-inflammatory action based on the excellent VLA-4 inhibitory action (International Publication WO2002/053534).

(1)

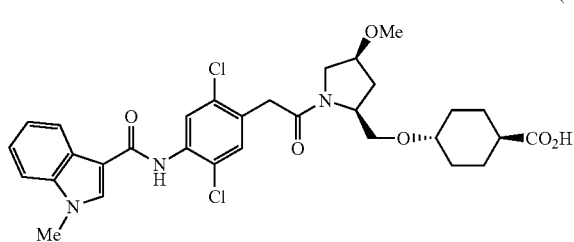

Compound (12) [a compound wherein $R^1$ is hydrogen atom in Compound (VI-trans)] is an important intermediate in producing such Compound (1).

(12)

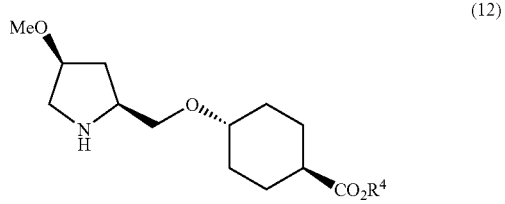

This compound has been synthesized by forming methylether structure at primary hydroxy group of hydroxypurine by Mitsunobu reaction; converting carboxylic acid moiety to hydroxymethyl group; introducing benzoic acid unit; reducing benzene ring of the benzoic acid moiety to obtain 1,4-cyclohexanecarboxylic acid ester comprising predominantly cis form; and conducting isomerization reaction via enolate (International Publication WO2002/053534).

Mitsunobu reaction, however, requires use of an azo reagent which is associated with the risk of explosion, and a large amount of unnecessary products are generated deriving from the reagents used in the reaction, requiring additional purification for the removal of such products. Accordingly, this method has many drawbacks for use in a mass synthesis. Furthermore, the reduction of benzene ring produces predominantly cis form product, and the step of isomerization was necessary to obtain the trans form. However, since the step of isomerization reaction required long time, hydrolysis of the ester occurred under the isomerization reaction conditions to produce a carboxylic acid as a byproduct. Accordingly, re-esterification of the carboxylic acid was necessary.

As described above, the conventional process required multiple Mitsunobu reaction step for the production of the Compound (1) rendering the process unfit for the large scale production. Furthermore, generation of the byproduct by the hydrolysis during the isomerization reaction also leaves much to be improved for use in an industrial production process.

SUMMARY OF THE INVENTION

The inventors of the present invention made an intensive experimental study and found that, in producing the important intermediate compound represented by formula (VI-trans), selection of benzyloxycarbonyl group for the protective group of $R^{11}$ enables conversion in the presence of a base into Compound (II) wherein $R^3$ is paratoluenesulfonyl group or methanesulfonyl group, and subjecting the thus obtained Compound (II) to SN-2 reaction with Compound (III) enables conversion into the desired Compound (IV); and that such process can avoid use of the Mitsunobu reaction, that $R^2$ does not have to be a protective group in such reaction process, and that the reaction can be promoted without using the protective group.

In addition, in the conventional process, the reduction of the compound (V) predominantly produced cis form compound, and isomerization of such cis form compound into trans form compound was necessary. The isomerization, however, required a longtime (see International Publication WO2002/053534). The inventors of the present invention, however, discovered that such isomerization can be accomplished in an extremely reduced period of time when an aprotic polar solvent such as N,N-dimethylformamide is used for the solvent, and also, that use of such solvent not only reduces the reaction time but also suppresses the carboxylic acid by-production by the hydrolysis of the ester, thereby enabling omission of the re-esterification step.

These remarkable improvements enable an efficient production of the compound (VI-trans) which is an important intermediate in producing the Compound (1). The present invention has been completed on the bases of such findings.

Accordingly, this invention relates to a process for producing a compound represented by formula (IV) as described below comprising the steps of reacting a compound represented by formula (I):

(I)

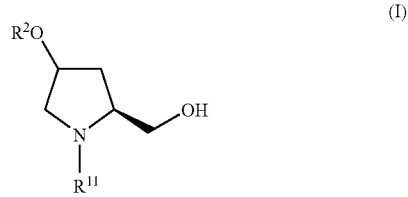

wherein $R^{11}$ represents a protective group of amino group, and $R^2$ represents hydrogen atom or a protective group of hydroxy group (with the proviso that when both $R^{11}$ and $R^2$ are protective groups, they are not the same protective group) with an optionally substituted arylsulfonyl chloride or an optionally substituted alkylsulfonyl chloride in the presence of a base to produce a compound represented by formula (II):

(II)

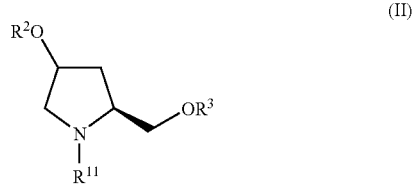

wherein $R^{11}$ and $R^2$ are as defined above, and $R^3$ represents an optionally substituted arylsulfonyl group or an optionally substituted alkylsulfonyl group; reacting this compound with the compound represented by formula (III):

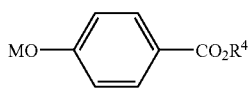

(III)

wherein $R^4$ is an optionally substituted alkyl group or an optionally substituted aralkyl group, and M represents an alkaline metal atom to obtain the compound represented by formula (IV):

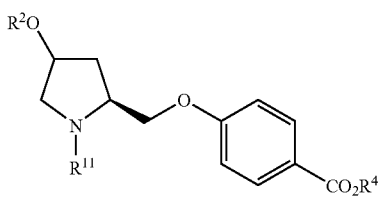

(IV)

wherein $R^{11}$, $R^2$, and $R^4$ are as defined above.

This invention also relates to:

each process as described above in which $R^{11}$ is benzyloxycarbonyl group;

each process as described above in which $R^2$ is hydrogen atom;

each process as described above in which $R^3$ is paratoluenesulfonyl group or methanesulfonyl group; and the process as described above in which $R^4$ is methyl group or ethyl group.

This invention also relates to a process for producing a compound represented by formula (VI-trans) as described below comprising the steps of reducing a compound represented by formula (V):

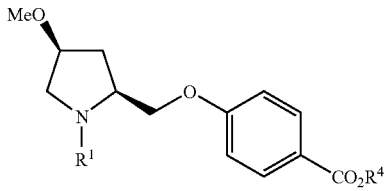

(V)

wherein $R^1$ represents hydrogen atom or a protective group of amino group, and $R^4$ is as defined above to produce a compound represented by formula (VI):

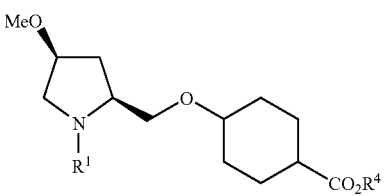

(VI)

wherein $R^1$ and $R^4$ are as defined above; treating this compound with a metal hydride in an aprotic polar solvent; and separating isomers to obtain the compound represented by formula (VI-trans):

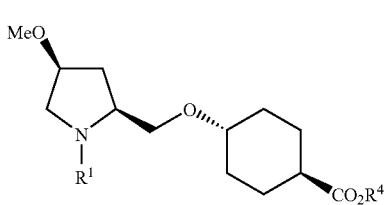

(VI-trans)

wherein $R^1$ and $R^4$ are as defined above.

This invention also relates to:

the process as described above in which $R^1$ is tertiary butoxycarbonyl group;

the process as described above in which $R^4$ is methyl group or ethyl group;

the process as described above in which the metal hydride is sodium hydride or lithium hydride; and the process as described above in which the aprotic polar solvent is N,N-dimethylformamide, N-methyl-2-pyrrolidone, or dimethylsulfoxide.

This invention also relates to a process for producing a compound represented by formula (1):

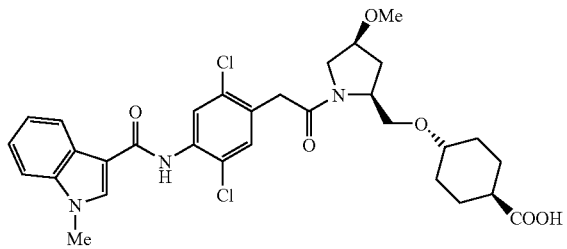

(1)

comprising the steps of condensing a compound represented by formula (12):

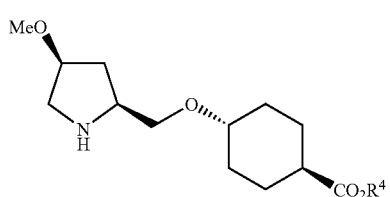

(12)

wherein $R^4$ represents an optionally substituted alkyl group or an optionally substituted aralkyl group with a compound represented by formula (20):

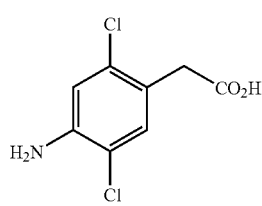

(20)

to produce a compound represented by formula (21):

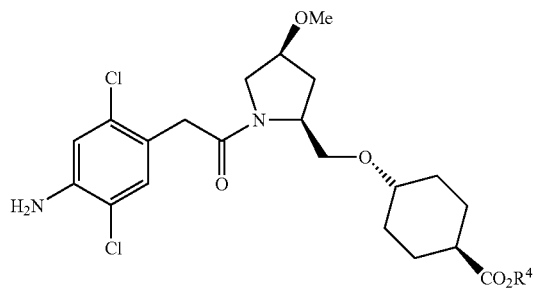
(21)

wherein R⁴ is as defined above; reacting this compound with a compound represented by the following formula (19):

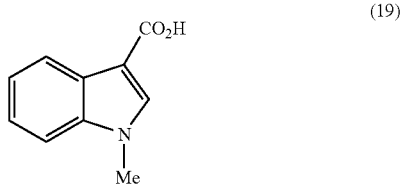
(19)

or its reactive derivative to produce a compound represented by formula (13):

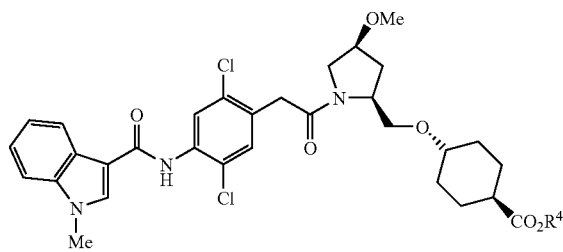
(13)

wherein R⁴ is as defined above; and cleaving ester group of this compound to produce the compound represented by formula (1).

This invention also relates to a compound represented by the following formula (21):

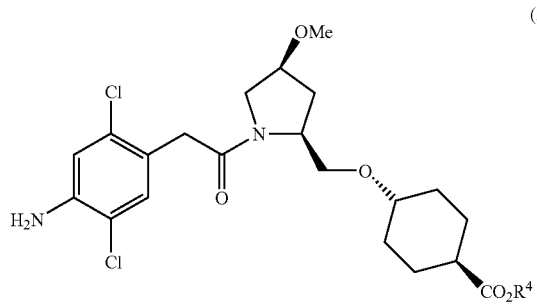
(21)

wherein R⁴ represents an optionally substituted alkyl group or an optionally substituted aralkyl group.

The production process and the intermediate of the present invention enables production of the Compound (1) exhibiting an excellent VLA-4 inhibitory action and a high safety at a high purity required for a pharmaceutical product and at a high efficiency.

BEST MODE FOR CARRYING OUT THE INVENTION

Next, the present invention is described in further detail.

One preferred embodiment of the present invention is the reaction process shown in the following reaction scheme starting from hydroxyproline. This process is accomplished without protecting the hydroxy group of the hydroxyproline, and accordingly, it is the feature of the process of the present invention that the conversion of the compound is enabled without protecting the hydroxy group of the hydroxyproline. However, an equivalent conversion can of course be accomplished with the hydroxy group protected. In such as case, the protective group employed may be selected from those commonly used in the art, and preferably, the protective group is the one different from the protective group on the nitrogen group of the hydroxyproline ring.

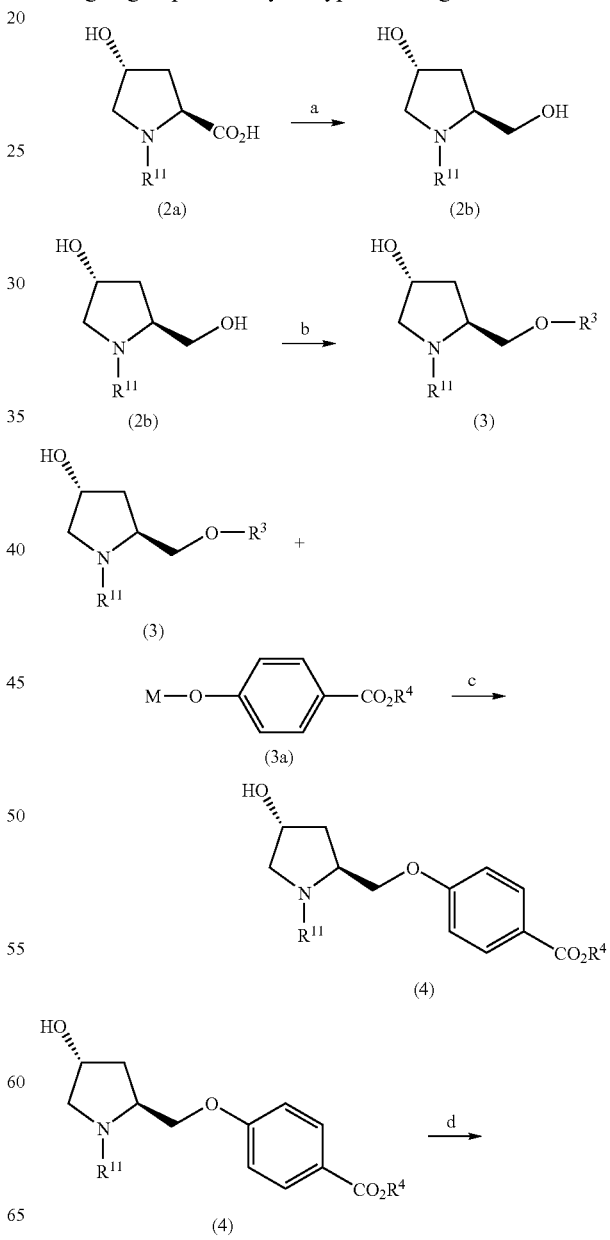

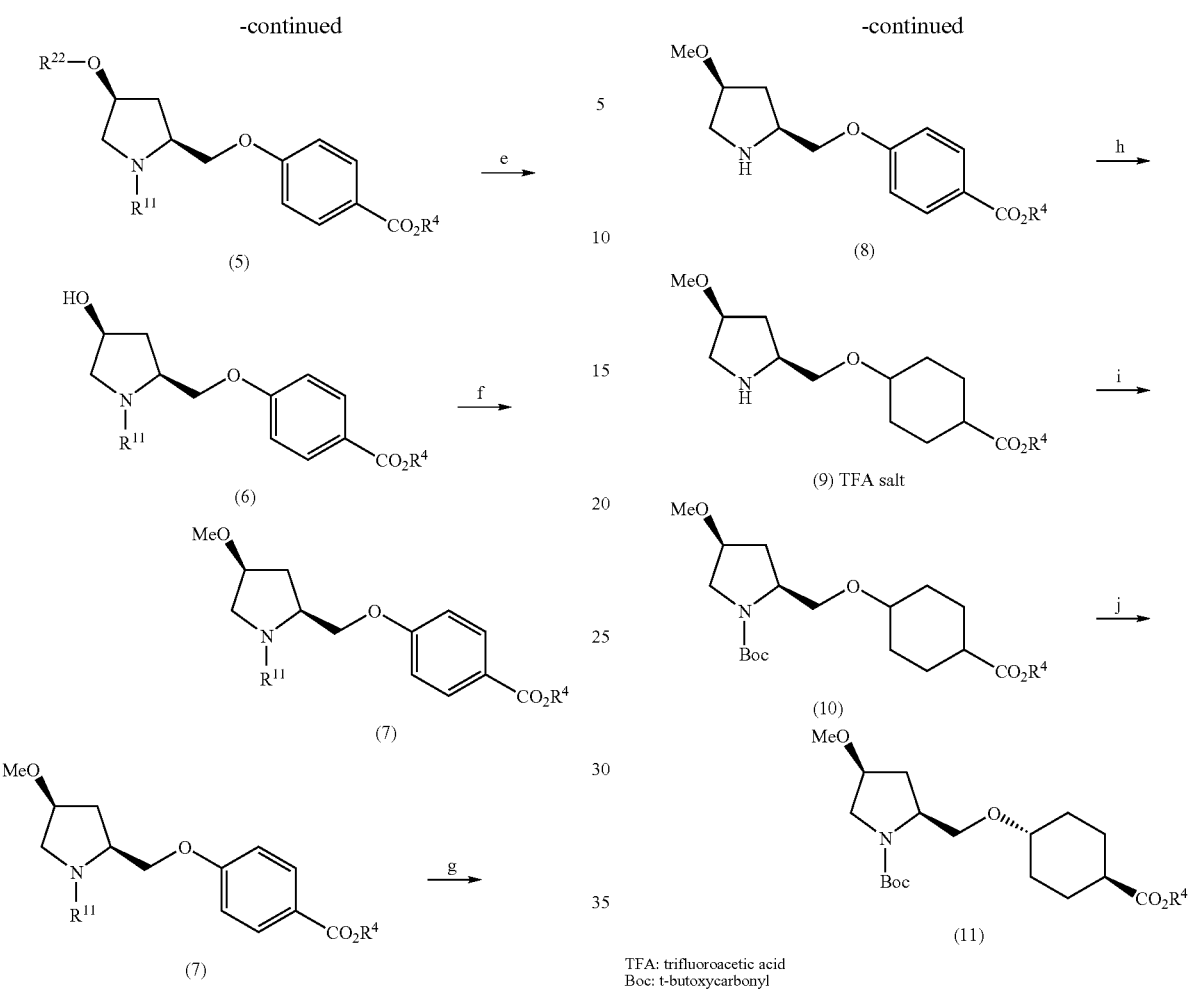
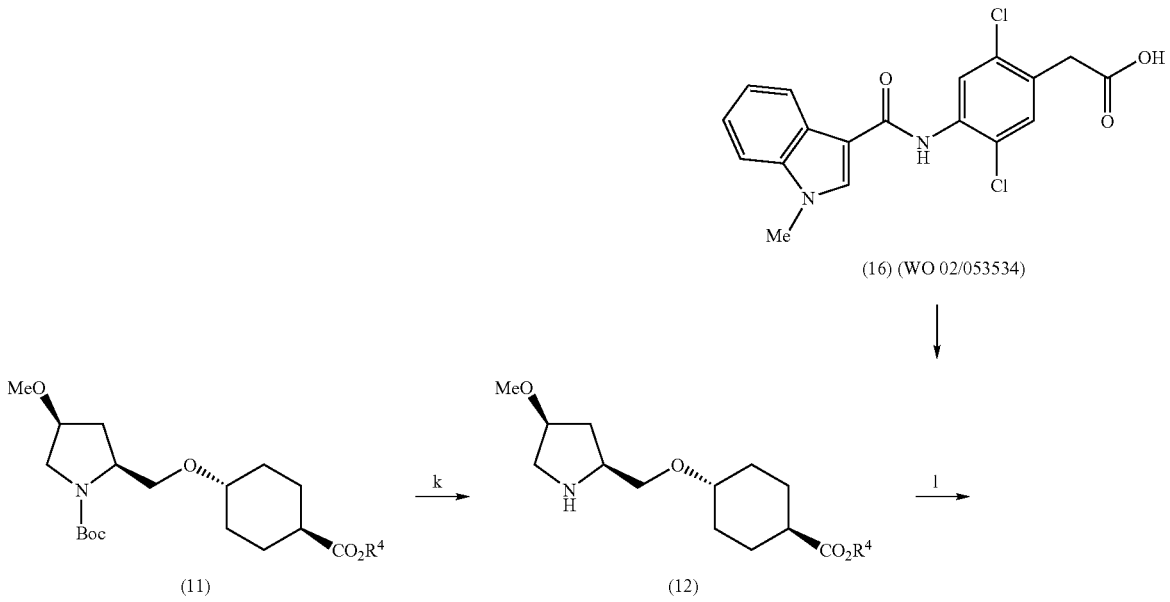
TFA: trifluoroacetic acid
Boc: t-butoxycarbonyl

-continued

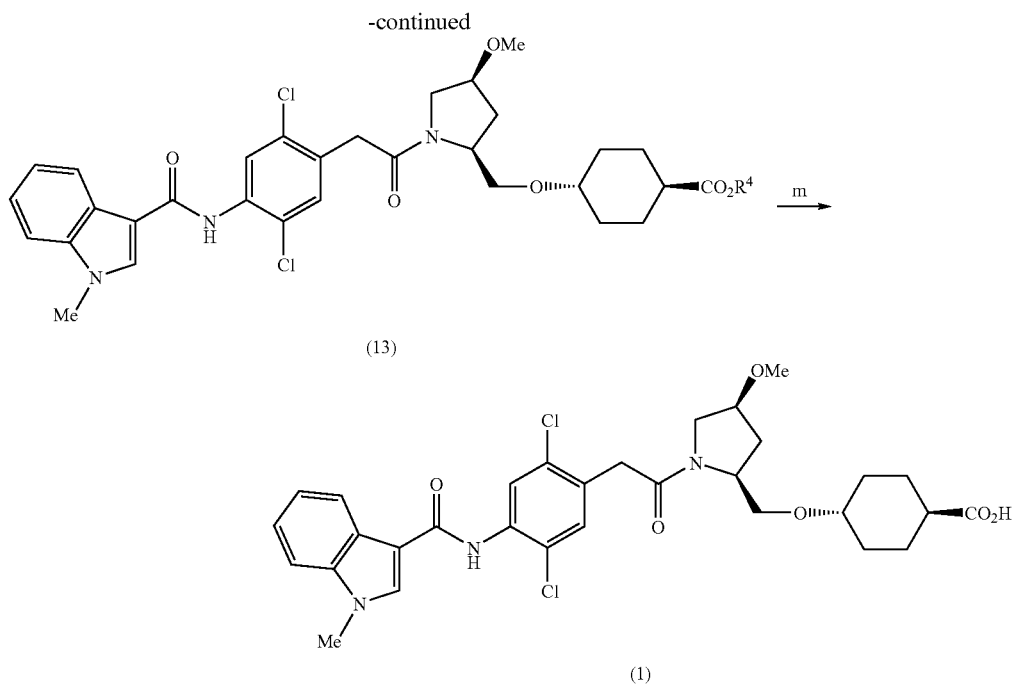

(13)

(1)

Next, each of these steps is described in further detail.

[Step a]

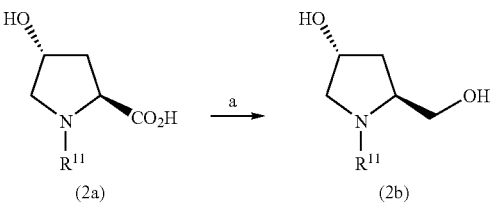

In this step, carboxyl group of Compound (2a) is converted to hydroxymethyl group.

In the formula, $R^{11}$ is the protective group of nitrogen atom (amino group). (With regard to the protective group, see, for example, "Protective Groups in Organic Synthesis", T. W. Greene and P. G. Wuts ed., John Wiley & Sons, Inc., New York, 1991.) Exemplary protective groups include carbonate, acyl, alkyl, and aralkyl protective groups, and the preferred are carbonate protective groups such as substituted or unsubstituted benzyloxycarbonyl groups such as benzyloxycarbonyl group and alkyloxycarbonyl groups such as tertiary butoxycarbonyl group. Among these, the most preferred is benzyloxycarbonyl group.

The conversion of the carboxyl group to the hydroxymethyl group may be accomplished by the known reduction method commonly used in the art (see, for example, International Publication WO2002/053534) to thereby produce Compound (2b). The simplest, however, is the reaction using a reducing agent, and a suitable reducing agent would be diborane. The diborane may be generated at the time of the reaction, or alternatively, it maybe a borane complex such as a commercially available borane-dimethyl sulfide complex (for example, Fieser and Fieser's Reagents for Organic Synthesis, 15, 44).

The solvent used in the reduction by diborane is not particularly limited as long as the reaction is not inhibited by the solvent. Exemplary solvents include hydrocarbon solvents such as toluene, and ethereal solvents such as diethylether and tetrahydrofuran, and the preferred is the use of an ethereal solvent such as tetrahydrofuran.

The reaction temperature used may be in the range of −78° C. to the boiling point of the solvent, and preferably, in the range of 0° C. to the boiling point of the solvent.

The reaction time may be in the range of 5 minutes to 24 hours. However, the reaction will normally be completed in about 30 minutes to 5 hours.

When Compound (2a) is produced, the reaction solution may be treated by a method commonly used in the art, and the compound may be isolated by the method commonly used in the art.

[Step b]

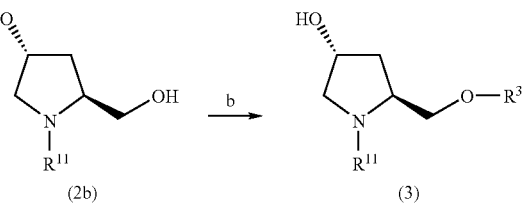

In this step, the hydroxymethyl group is converted to a substituted sulfonyl oxy group, and the hydroxy group is converted to a leaving group for use in the replacement reaction. The leaving group is not limited to the substituted sulfonyl oxy group, and any substituent which can fulfil the role of the leaving group such as a halogen atom may be used. However, use of the substituted sulfonyloxy group is the simplest and the most preferred.

In the formula, $R^{11}$ is as defined above. $R^3$ is a substituted sulfonyl group such as a substituted or unsubstituted arylsulfonyl group or a substituted or unsubstituted alkylsulfonyl group. The substituted sulfonyl group is preferably p-toluenesulfonyl group or methanesulfonyl group.

The starting Compound (2b) has one secondary hydroxy group and one primary hydroxy group, and the primary hydroxy group of the hydroxymethyl group can be selectively converted to the substituted sulfonyloxy group by adjusting the amount of the reagents and the reaction temperature used. The reaction can be promoted by reacting Compound (2b) with a substituted sulfonyl halogenide, and preferably substituted sulfonyl chloride in the presence of a base by the procedure as described below.

The substituted sulfonyl halogenide used may be the one corresponding to the sulfonyl employed, and examples are p-toluenesulfonyl chloride and methanesulfonyl chloride, which may be used at an amount 1 to 2.5 molar equivalents, and preferably 1 to 1.5 molar equivalents of the Compound (2b).

Exemplary bases that may be used include organic bases such as triethylamine, N,N-dimethylaniline, pyridine, 4-dimethylaminopyridine, and other alkyl amines, aromatic amines, and nitrogen-containing heterocyclic compounds; and inorganic bases such as carbonate and hydrogencarbonate of an alkaline metal or an alkaline earth metal such as anhydrous potassium carbonate, anhydrous sodium carbonate, and sodium hydrogencarbonate. The preferred is an organic base such as triethylamine or 4-dimethylaminopyridine. These bases may be used at an amount of 1 to 10 equivalents, and preferably 1 to 2.5 equivalents of the Compound (2b), and at an equimolar amount with the substituted sulfonyl halogenide used.

The reaction solvent is not particularly limited as long as the reaction is not inhibited by the solvent. Examples include toluene and other hydrocarbon solvent, diethylether, tetrahydrofuran, and other ethereal solvent, and methylene chloride, 1,2-dichloroethan and other chlorinated solvents. Among these, the preferred are chlorinated solvents such as methylene chloride and 1,2-dichloroethane.

The reaction temperature used may be in the range of −78° C. to the boiling point of the solvent, and preferably, in the range of 0° C. to the room temperature.

The reaction time may be in the range of 5 minutes to 24 hours. However, the reaction will normally be completed in about 30 minutes to 6 hours.

Compound (3) is generally produced as an unstable compound. However, as long as its formation is instrumentally confirmed and its purity is at a sufficient level, the product can be used in the subsequent step with no further isolation or purification.

[Step c]

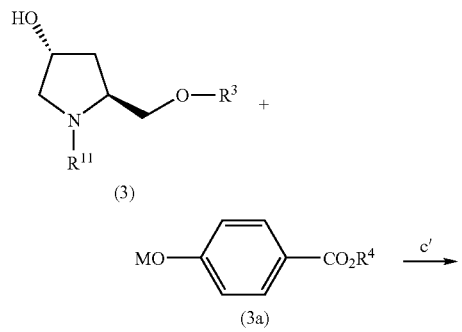

(3)

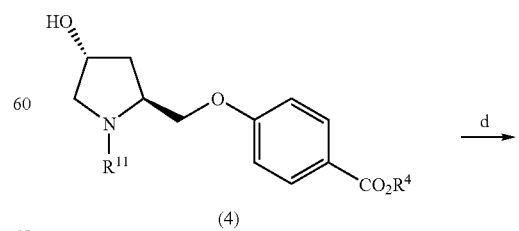

(3a)

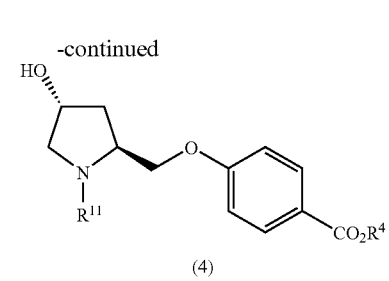

(4)

In this step, benzoic acid unit is introduced in Compound (3).

This introduction of the benzoic acid unit is accomplished by using 4-hydroxybenzoate, whose methyl and ethyl esters, for example, are commercially available. The benzoic acid compound is converted to a sodium, potassium, or lithium phenolate derivative, or further to a calcium phenolate derivative, and this derivative and the Compound (3) maybe subjected to a coupling reaction. This reaction is a common reaction of a phenolate anion well known to form an arylether bond. Accordingly, the metal atom (cation) represented by M in the compound of formula (III) may be a metal atom selected from alkaline metal atoms and alkaline earth metal atoms, and preferably, an alkaline metal atom, and more preferably lithium, sodium, or potassium, and most preferably sodium or potassium.

The solvent used is not limited as long as the reaction is not inhibited by the solvent. Examples include toluene and other hydrocarbon solvents, diethylether, tetrahydrofuran, and other ethereal solvent, and N,N-dimethylformamide, N-methyl-2-pyrrolidone, dimethylsulfoxide and other aprotic polar solvents. Among these, the preferred include tetrahydrofuran and N,N-dimethylformamide, and the solvent used is preferably anhydrous to the extent commonly used in the art.

In such a solvent, an inorganic base such as carbonate, hydrogencarbonate, or the like of an alkaline metal or an alkaline earth metal, for example, anhydrous potassium carbonate, anhydrous sodium carbonate, or sodium hydrogencarbonate and Compound (3) may be added to the commercially available 4-hydroxybenzoate to carry out the reaction. Alternatively, 4-hydroxybenzoate may be pretreated with a metal hydride to form a phenolate before adding the Compound (3).

The reaction temperature used may be in the range of 0° C. to the boiling point of the solvent, and preferably, in the range of 20° C. to 120° C.

The reaction time may be in the range of 30 minutes to 24 hours. However, the reaction will normally be completed in about 30 minutes to 4 hours.

This reaction is preferably conducted under anhydrous conditions to thereby avoid hydrolysis of the ester group and decomposition of the sulfonyloxy form (3).

[Step d] and [Step e]

(4)

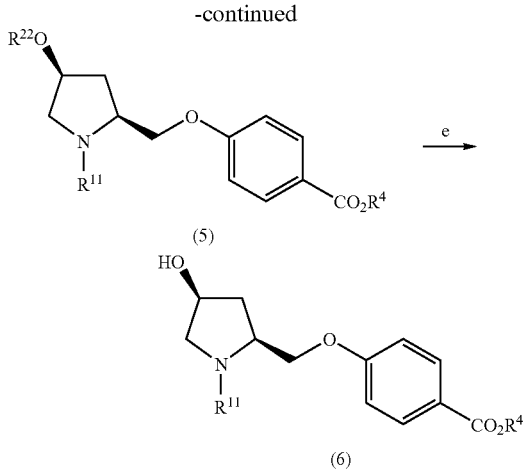

In these steps, configuration of the hydroxy group present as a substituent on the ring is converted from α to β (or the configuration of the carbon atom to which the hydroxy group is bonded is converted from R configuration to S configuration). More specifically, in these steps, Compound (4) having hydroxy group is converted by using Mitsunobu reaction to ester form or formyl form (5) wherein the hydroxy group has undergone stereospecific conversion (Step d), and then, the substituent (protective group) $R^{22}$ is selectively removed (Step e). These steps enable production of Compound (6) in which the configuration of the hydroxy group has been converted from α to β. These steps of conversion can be readily carried out by the methods known in the art (International Publication WO2001/00206 and International Publication WO2002/053534).

In the formula, $R^{11}$ and $R^4$ are as defined above, and $R^{22}$ represents an unsubstituted or substituted aroyl group, an alkanoyl group, or formyl group, and preferably, 4-nitrobenzoyl group, benzoyl group, acetyl group, or formyl group. Among these, $R^{22}$ is most preferably 4-nitrobenzoyl group, acetyl group, or formyl group.

Exemplary carboxylic acids which may be used in [Step d] include 4-nitrobenzoic acid, benzoic acid, acetic acid, and formic acid, and preferred are 4-nitrobenzoic acid and formic acid.

An exemplary phosphine reagent used in the reaction is triphenylphosphine.

The reaction solvent is not particularly limited as long as the reaction is not inhibited by the solvent. Examples include toluene and other hydrocarbon solvent, and diethylether, tetrahydrofuran, and other ethereal solvent. Among these, the preferred is tetrahydrofuran.

Exemplary azo reagents used include commercially available azodicarboxylic acid esters such as diisopropyl azodicarboxylate and diethyl azodicarboxylate.

The reaction temperature used may be in the range of 0° C. to the boiling point of the solvent.

Compound (5) can be purified by column chromatography using silica gel or the like. Alternatively, the Compound (5) may be used without purification and separated and purified after completing the subsequent [Step e].

[Step e] is the step of deesterification or deformylation, and such reaction can be accomplished by a method in the art which can readily promote selective deesterification or deformylation by distinguishing the carboxylic acid ester group in the molecule.

More specifically, the ester may be cleaved by using an alcoholic solvent such as ethanol or methanol, or an ethereal solvent such as tetrahydrofuran, and preferably, by using tetrahydrofuran or ethanol. If desired, water may be added to the solvent at a stoichiometric amount to 10 molar equivalents.

The reaction temperature used may be in the range of 0° C. to the boiling point of the solvent, and preferably, in the range of 0° C. to the room temperature.

The reaction time may be in the range of 5 minutes to 24 hours. However, the reaction will normally be completed in about 30 minutes to 4 hours.

[Step f]

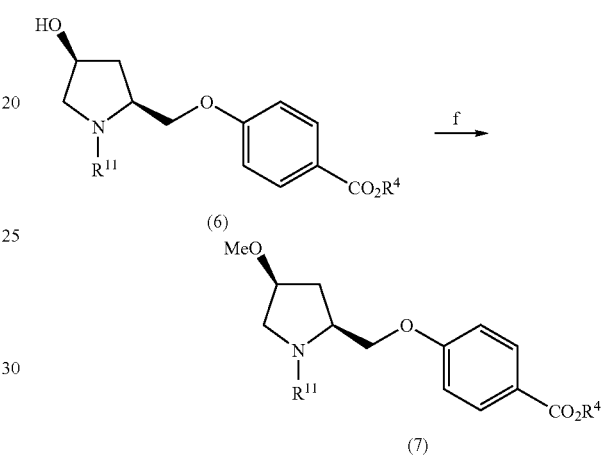

In this step, hydroxyl group on the ring is converted to methoxy group by introducing methyl group to the hydroxy group.

This step may be carried out by the method commonly used in the art for methylation of the hydroxy group, and more specifically, by treating the Compound (6) with a methylating reagent in the presence of a base.

Exemplary methylation reagents include methyl halides such as methyl iodide.

The base used is preferably a metal hydride, and use of sodium hydride or lithium hydride is preferred.

The reaction solvent is not particularly limited as long as the reaction is not inhibited by the solvent. Examples include toluene and other hydrocarbon solvent, diethylether, tetrahydrofuran, and other ethereal solvent, and N,N-dimethylformamide, N-methyl-2-pyrrolidone, dimethylsulfoxide and other aprotic polar solvents. Among these, the preferred include tetrahydrofuran and N,N-dimethylformamide, and the solvent used is preferably anhydrous to the extent commonly used in the art.

The reaction temperature used may be in the range of −78° C. to the boiling point of the solvent, and preferably, in the range of −20° C. to the room temperature.

The reaction time may be in the range of 30 minutes to 24 hours. However, the reaction will normally be completed in about 1 hour to 5 hours.

It is also to be noted that this step is preferably conducted under anhydrous conditions, and more preferably, in nitrogen stream to thereby prevent cleavage of the ester and decomposition of $R^1$ which is the protective group of the nitrogen atom in the pyrrolidine ring.

[Step g]

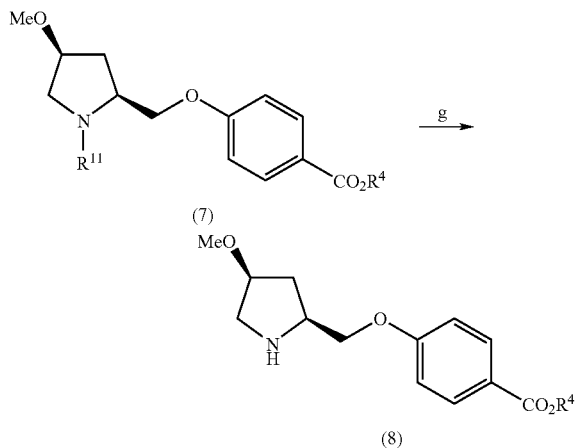

In this step, the protective group on the nitrogen atom is removed. This removal of the protective group is particularly desirable when the protective group on the Compound (7) is a protective group containing an aromatic ring since the reaction in the following steps will be complicated if the aromatic ring in such protective group is reduced in the course of the reduction of the aromatic ring in the benzoic acid moiety conducted in the subsequent step. This step can be accomplished by a method commonly used in the art in removing the protective group on the nitrogen atom depending on the type of the selected protective group (for example, Protective Groups in Organic Synthesis, edited by T. W. Greene and P. G. Wuts, John Wiley & Sons, Inc., New York, 1991).

In the formula, $R^{11}$ and $R^4$ are as defined above.

For example, when $R^{11}$ is benzyloxycarbonyl group, the deprotection can be accomplished by catalytic hydrogenation under neutral conditions. The catalyst used may be a palladium catalyst such as palladium-carbon or palladium hydroxide (II) or a platinum catalyst such as platinum dioxide.

The reaction solvent is not particularly limited as long as the reaction is not inhibited by the solvent. Examples include alcoholic solvents such as ethanol and methanol, and ethereal solvents such as tetrahydrofuran, and the preferred at methanol and ethanol.

The reaction may be carried out at a hydrogen pressure in the range of normal pressure to 10 Mpa, and preferably at normal pressure to 1 Mpa.

[Step h] and [Step i]

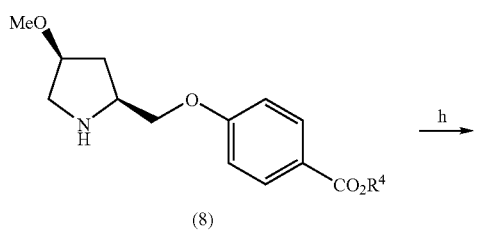

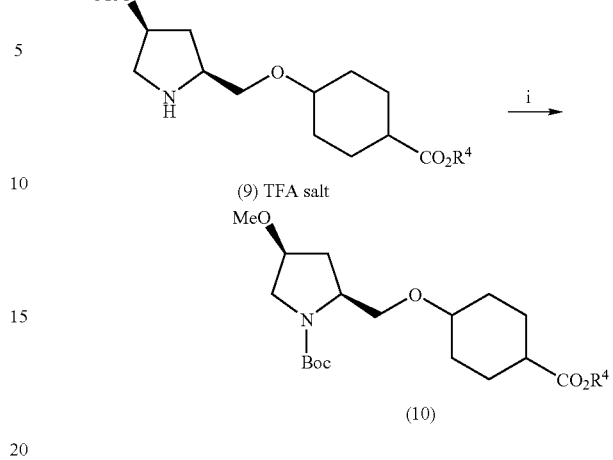

In this step, benzene ring moiety in the unit introduced as benzoic acid unit is reduced for conversion to cyclohexane ring.

In the formula, $R^4$ is as defined above.

This step can be accomplished by using a relatively mild method of the methods commonly known in the art for hydrogenation of benzene ring for conversion into cyclohexane ring. An exemplary such method is the method of W. M. Pearlman et al. (Organic Synthesis, Collective volume 5, page 670-672, John Wiley & Sons, Inc.). This reduction reaction is highly selective for cis form, and reported to be capable of predominantly producing the 1,4-cis form. In addition, this step can be smoothly carried out if this step is conducted after removing free nitrogen atom which is a catalytic poison inhibiting the reaction in the catalytic reduction step by converting it to a salt by adding an acid.

The subsequent introduction of tertiary butoxycarbonyl group protects the nitrogen atom, and such protection is advantageous for improving handling convenience in the subsequent steps (isomerization and isomer separation and purification). While introduction of the tertiary butoxycarbonyl group is described, the protective group introduced is not limited to the tertiary butoxycarbonyl group, and other protective groups can also be used as long as the group fulfils the same function. Exemplary such protective group is an optionally substituted benzyloxycarbonyl group.

The catalyst used in the step of the benzene ring hydrogenation may be commercially available palladium-carbon catalyst, platinum oxide catalyst, strontium carbonate catalyst, rhodium-alumina catalyst, or the like, and the most preferred is rhodium-alumina catalyst.

This step can be completed when the catalyst is used at an amount of 1% to 50% of the weight of the substrate to be reduced. The catalyst, however, is preferably used at 3% to 20% of the substrate.

The reaction solvent is not particularly limited as long as the reaction is not inhibited by the solvent. Examples include alcoholic solvents such as ethanol and methanol and ethereal solvents such as tetrahydrofuran and dioxane. The solvent is preferably an alcoholic solvent such as methanol or ethanol, and the solvent preferably has 5% to 20% by volume of acetic acid or trifluoroacetic acid added as co-solvent.

The reaction may be carried out at a hydrogen pressure in the range of normal pressure to 10 Mpa, and preferably at normal pressure to 1.5 Mpa.

The reaction temperature used may be in the range of 0° C. to 100° C., and preferably, in the range of 20° C. to 60° C.

The reaction time may be in the range of 1 hour to 72 hours. However, the reaction will normally be completed in about 2 hours to 48 hours.

The step of introducing tertiary butoxycarbonyl group, or other protective group may be accomplished by using a method commonly used in the art in protecting nitrogen atom (amino group) (Protective Groups in Organic Synthesis, eds. by T. W. Greene and P. G. Wuts, John Wiley & Sons, Inc., New York, 1991).

[Step j]

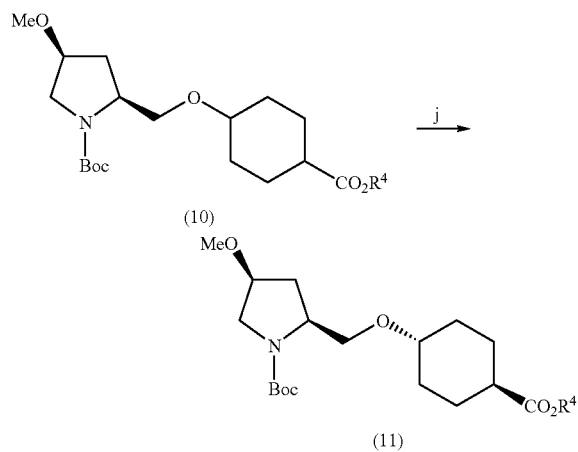

In this step, the cis isomer predominantly formed in the benzene ring-reducing step as described above is converted to trans isomer.

In the formula, $R^4$ is as defined above.

This step comprises the step of increasing the proportion of compound of the desired trans form configuration by isomerization of Compound (10) via enolate, and separating and purifying the two isomers. The carboxylic acid compound produced as a byproduct in the isomerization can be readily converted to the desired ester Compound (11) by conducting the re-esterification.

The isomerization reaction similar to this step has been conducted in the method described in International Publication WO2002/053534 by heating the compound of methylester form (10) wherein $R^4$ is methyl group in methanol under reflux for 15 hours to several days with stirring by using sodium methoxide for the base. However, in the investigation by the inventors of the present invention, it was found that, when the same reaction is conducted by changing the solvent to N,N-dimethylformamide or other aprotic polar solvent, the reaction temperature can be reduced to up to 50° C. and the isomerization reaction reaches its stationary state in a remarkably shorter time of 5 minutes to 1 hour although the time may somewhat vary depending on the type of the substrate.

This is quite advantageous since the isomerization reaction can be completed in a short time, and hence, production of the byproduct carboxylic acid can be minimized so that the step of re-esterification is no longer required.

In the improved reaction conditions, the reaction may be carried out by dissolving the starting material in an aprotic polar solvent such as N,N-dimethylformamide, N-methyl-2-pyrrolidone, or dimethylsulfoxide. In addition, the reaction is preferably carried out in the simultaneous presence of an alcohol corresponding to $R^4$ at an amount of 1 to 3 molar equivalents of Compound (10).

An exemplary base used is sodium hydride.

The reaction temperature used may be in the range of 0° C. to 50° C., and preferably, in the range of 0° C. to 25° C.

The base is then added while maintaining this temperature, and the stirring is continued at room temperature to 50° C. for 5 minutes to 1 hour while monitoring the reaction. The reaction is terminated and neutralized by adding diluted hydrochloric acid or the like with cooling.

The conversion of the byproduct carboxylic acid to the ester form (11) can be accomplished by the following treatments:

an esterificatin in which the reaction solvent used is an aprotic polar solvent such as N,N-dimethylformamide or N-methyl-2-pyrrolidone, and preferably N,N-dimethylformamide; the base used is anhydrous potassium carbonate or anhydrous sodium carbonate; and the alkylating agent is the corresponding $R^4$-bromide or $R^4$-chloride; and an esterification for the case when the ester is a methyl ester, using commercially available trimethylsilyldiazomethane in diethylether or benzene-methanol mixed solvent (4:1, v/v).

In this isomerization reaction, production of the byproduct carboxylic acid during the hydrolysis is reduced, and the decrease in the yield of the isolated Compound (11) was as low as 10% or less when the step of re-esterification was omitted. The separation and purification of the trans form Compound (11) can be accomplished by the ordinary column chromatography using silica gel, and the separation can be accomplished at a high efficiency if a commercially available medium pressure preparative column separator is used. Separation may also be conducted by other means such as HPLC.

[Step k]

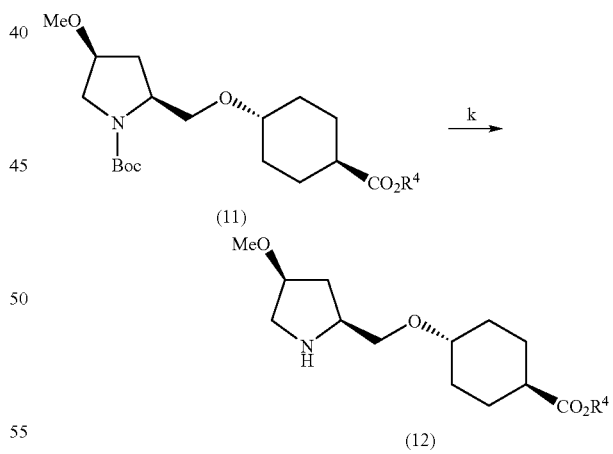

In this step, the protective group on the nitrogen atom is removed.

In the formula, $R^4$ is as defined above.

This step may be accomplished by a known method used in removing tertiary butoxycarbonyl group which is a protective group on the nitrogen atom (Protective Groups in Organic Synthesis, eds. by T. W. Greene and P. G. Wuts, John Wiley & Sons, Inc., New York, 1991), and the protective group other than the tertiary butoxycarbonyl group can also be removed by a similar method. For example, in the case of the tertiarybutoxycarbonyl group, Compound (12) can be deprotected by using commercially available 4N hydrochloric acid-dioxane or trifluoroacetic acid, and in the case of trifluoroacetic acid, chlorinated solvent such as methylene chloride can be used as co-solvent solvent.

The reaction temperature used may be in the range of 0° C. to the boiling point of the solvent.

The reaction time may be in the range of 5 minutes to 24 hours. However, the reaction will normally be completed in about 30 minutes to 5 hours.

When the reaction solvent is distilled off after the completion of the deprotection reaction, Compound (12) is isolated as a salt with the acid employed, for example, as a hydrochloride or a trifluoroacetate. These salt can be used as they are in the subsequent reaction, or they may be isolated as the Compound (12) in free amine form by neutralization using a saturated solution of sodium bicarbonate or the like.

The thus produced Compound (12) can be converted to Compound (13) by condensation according to a known method, for example, a method described in International Publication WO2002/053534 with Compound (20) which can be produced by the method described in the same publication.

The step from Compound (13) to Compound (1) can be accomplished by a known method used in cleaving the ester form (Protective Groups in Organic Synthesis, eds. by T. W. Greene and P. G. Wuts, John Wiley & Sons, Inc., New York, 1991) to convert into a free carboxylic acid.

Compound (13) can also be produced by the following method.

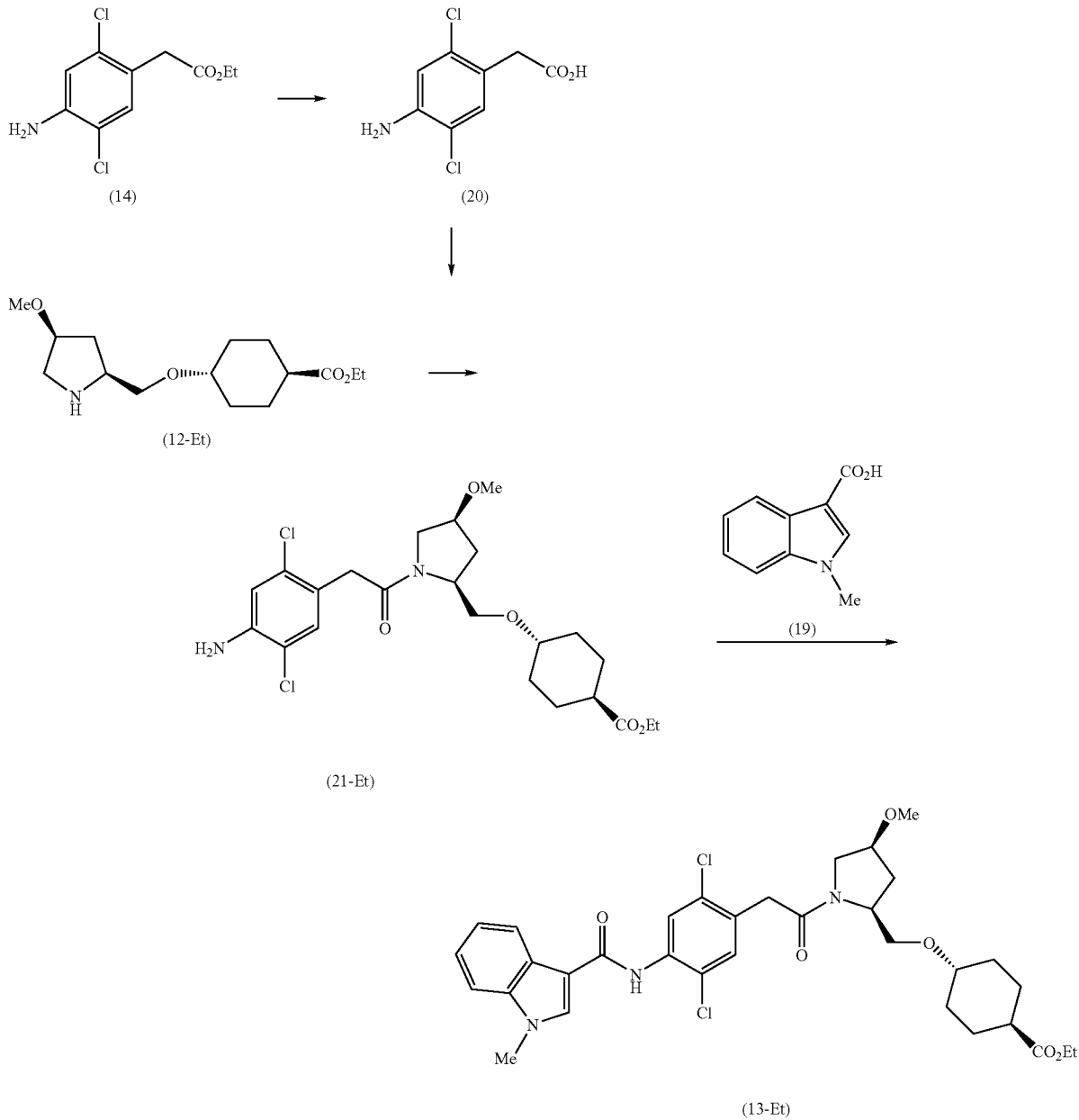

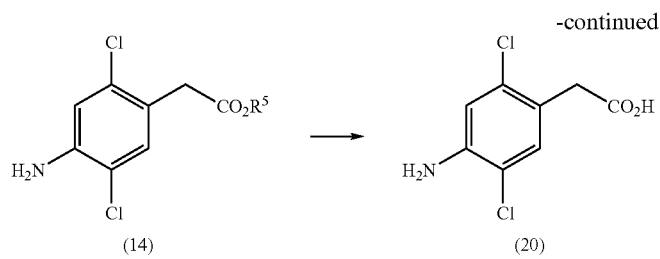

In the formula, R[5] represents a straight chain or branched alkyl group or a substituted or unsubstituted arylalkyl group, and preferably methyl group, ethyl group, tertiary butyl group, benzyl group, or 4-methoxybenzyl group, and most preferably methyl group or ethyl group. This step is a common reaction of producing a free carboxylic acid by the hydrolysis of an ester, which can be accomplished by a method commonly used in the art in converting an alkoxy carbonyl group to a carboxylic acid (Protective Groups in Organic Synthesis, eds. by T. W. Greene and P. G. Wuts, John Wiley & Sons, Inc., New York, 1991).

The reaction temperature used may be in the range of −20° C. to the boiling point of the solvent, and preferably, in the range of 0° C. to the room temperature.

This reaction may also be conducted in the presence of an organic amine base such as triethylamine or N,N-dimethylaminopyridine, or in the presence of an organic amine and an active esterifying reagent such as 1-hydroxybenzotriazole at a catalytic amount to stoichiometrically equivalent amount.

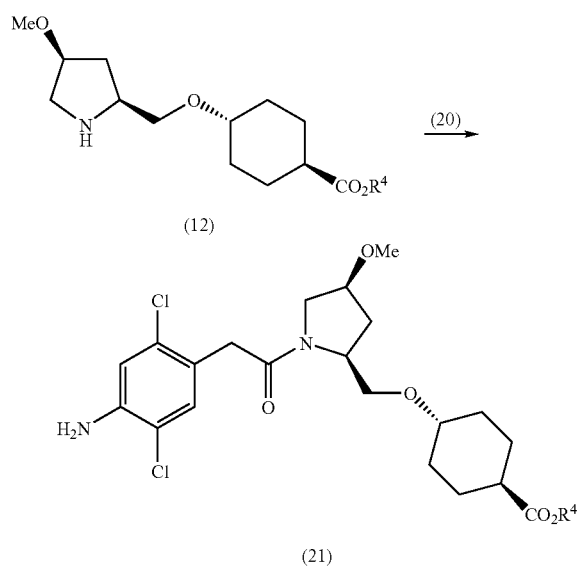

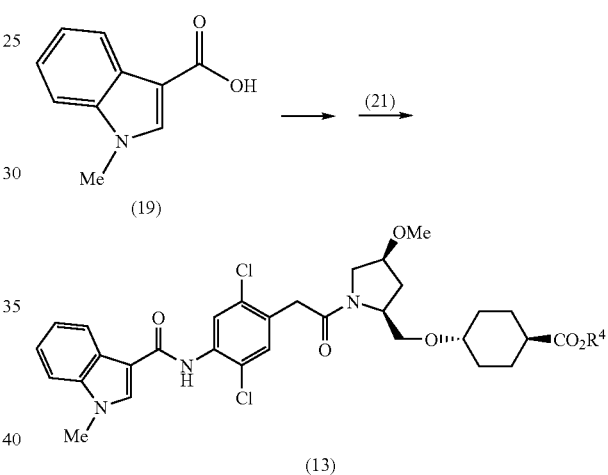

In the formula, R[4] is as defined above.

This step is condensation of Compound (12) with Compound (20), which can be readily accomplished by a method known in the art.

The reaction solvent is not particularly limited as long as the reaction is not inhibited by the solvent. Examples include methylene chloride and other halogenated hydrocarbon solvents, toluene and other hydrocarbon solvents, tetrahydrofuran and other ethereal solvents, and N,N-dimethylformamide, N-methyl-2-pyrrolidone, and other aprotic polar solvents. Among these, the preferred are methylene chloride and N,N-dimethylformamide.

The reaction can be accomplished in such a solvent by using a condensing agent such as 1-ethyl-3-(3-dimethylaminopropyl)carbodiimide hydrochloride, N,N-dicyclohexylcarbodiimide, N,N-carbonyldiimidazole, or an analog thereof. The reaction is preferably conducted in N,N-dimethylformamide by using 1-ethyl-3-(3-dimethylaminopropyl)carbodiimide hydrochloride, or N,N-dicyclohexylcarbodiimide.

In the formula, R[4] is as defined above.

Compound (13) can be produced by condensing Compound (19) or a reactive derivative such as an acid halide (for example, acid chloride) of this compound with Compound (21) by a known condensing reaction.

The solvent used in the conversion of a commercially available 1-methyl-3-indolcarboxylic acid (19) to, for example, an acid chloride may be a chlorinated solvent such as methylene chloride or 1,2-dichloroethane, a hydrocarbon solvent such as toluene or benzene, or an ethereal solvent such as tetrahydrofuran. The solvent is preferably a chlorinated solvent such as methylene chloride or 1,2-dichloroethane.

The reaction temperature used may be in the range of 0° C. to the boiling point of the solvent.

The chlorinating agent used may be the one commonly used in the art in converting a carboxylic acid such as oxalyl chloride and thionyl chloride to an acid chloride.

The solvent used in the condensation step of the acid chloride of Compound (19) with Compound (21) may be, for example, a chlorinated solvent such as methylene chloride or 1,2-dichloroethane, a hydrocarbon solvent such as toluene or benzene, or an ethereal solvent such as tetrahydrofuran. Preferably, the solvent is a chlorinated solvent such as methylene chloride.

The reaction temperature used may be in the range of 0° C. to the boiling point of the solvent, and preferably, in the range of room temperature to the boiling point of the solvent.

The base used may be, for example, a stoichiometric amount of an organic base such as triethylamine.

This step is effective in synthesizing a derivative having the 1-methyl-3-indolcarboxylic acid moiety labeled with an isotope, in synthesizing an active metabolite, or in synthesizing a compound having 1-methyl-3-indolcarboxylic acid moiety modified. In addition, Compound (21) is a novel compound, and this compound is useful as an intermediate for synthesizing not only Compound (1) but also a compound having VLA-4 inhibitory action such as Compounds (1a) to (1f) as shown below which are useful biologically active substances.

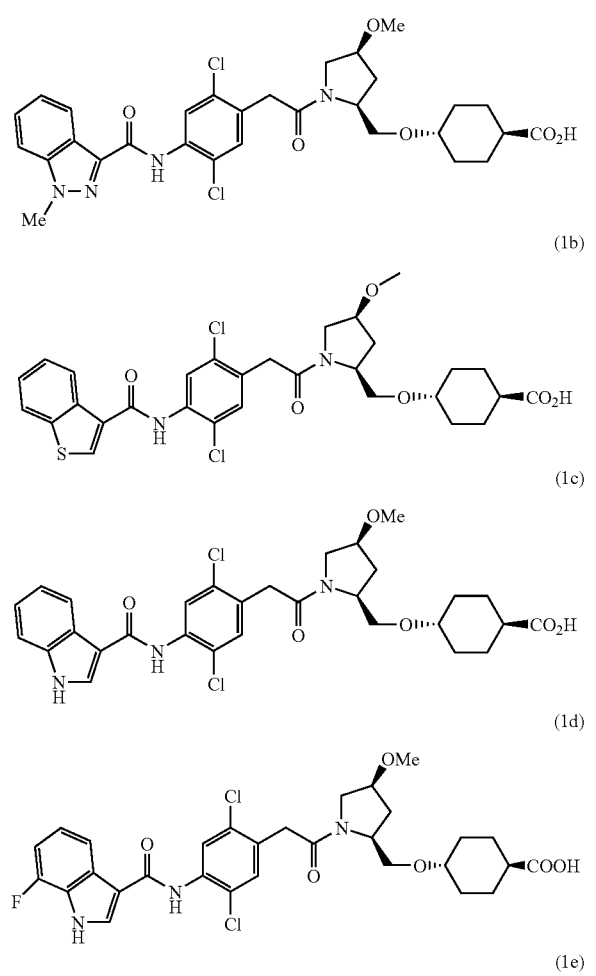

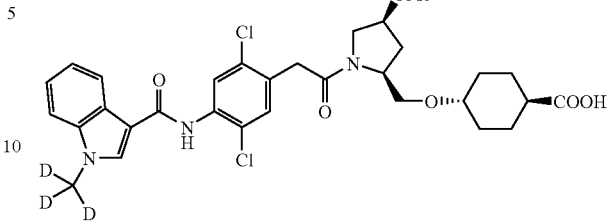

The resulting ester of Compound (13) can be cleaved into a free carboxylic acid by hydrolysis, catalytic hydrogenation, or other known process (Protective Groups in Organic Synthesis, eds. by T. W. Greene and P. G. Wuts, John Wiley & Sons, Inc., New York, 1991) to thereby produce Compound (1).

EXAMPLES

Next, the present invention is described in further detail by referring to the Examples which by no means limit the scope of the present invention.

Reference Example 1

2,5-dichloro-4-[(1-methyl-1H-indol-3-yl)carboxamido]phenylacetic acid

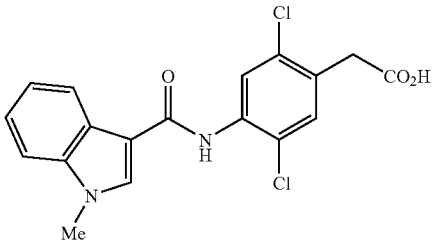

1-methyl-1H-indole-3-carboxylic acid (794 mg, 4.53 mmol) was dissolved in methylene chloride (25 ml), and oxalyl chloride (0.79 ml, 9.1 mmol) was added at 0° C. with stirring. The reaction mixture was stirred at room temperature for another 1 hour, and the reaction mixture was exsiccated under reduced pressure. The residue was dissolved in methylene chloride (25 ml), and a solution of triethylamine (0.84 ml, 9.0 mmol) and ethyl 4-amino-2,5-dichlorophenylacetate (750 mg, 3.02 mmol) in methylene chloride (5 ml) was added at 0° C. with stirring. The reaction mixture was heated under reflux with stirring for 18 hours. After cooling the reaction mixture, water (30 ml) was added and the solution was extracted with chloroform. The extract was washed with saturated sodium chloride solution and dried over anhydrous magnesium sulfate, and the solvent was distilled off under reduced pressure. The resulting residue was purified by column chromatography using silica gel (medium pressure HPLC manufactured by Yamazen Corporation; chloroform: methanol, 100:0 to 95:5 (v/v)), and to the resulting ethyl 2,5-dichloro-4-[(1-methyl-1H-indol-3-yl)carboxamido]phenylacetate in ester form with no further purification were added tetrahydrofuran (THF; 45 ml) and 0.25N NaOH (18 ml, 4.5 mmol). The resulting mixture was stirred at room temperature for 4 hours. While cooling the reaction mixture, 1N HCl was gradually added to the reaction mixture to render the pH weakly acidic to thereby collect precipitated crystals. The crystals was washed with water, and dried to give the title compound (807 mg, 71%) as a crystal powder.

MS (ESI); m/z: 378 (M$^+$+2).

$^1$H-NMR (DMSO-d$_6$) δ: 3.72 (s, 2H), 3.90 (s, 3H), 7.22 (t, J=8.1 Hz, 1H), 7.28 (t, J=8.1 Hz, 1H), 7.56 (d, J=8.3 Hz, 1H), 7.64 (s, 1H), 7.92 (s, 1H), 8.15 (d, J=7.8 Hz, 1H), 8.31 (s, 1H), 9.39 (s, 1H).

Example 1

Benzyl (4R)-hydroxy-(2S)-hydroxymethylpyrrolidine-1-carboxylate

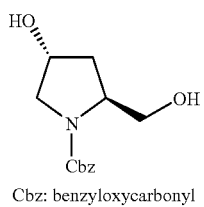

Cbz: benzyloxycarbonyl

N-benzyloxycarbonyl-(4R)-hydroxy-L-proline (150 g, 0.565 mol) was dissolved in THF (1.5 L), and borane-dimethyl sulfide complex (59.0 ml, 0.622 mol) was added dropwise to the solution with stirring at 0° C. After completing the addition, the reaction mixture was heated under reflux with stirring. After stirring for another 3 hours, the reaction mixture was again cooled to 0° C. Borane-dimethyl sulfide complex (16.1 ml, 0.170 mol) was added, and the reaction mixture was stirred for another 10 hours. After cooling the reaction mixture, water (500 ml) was gradually added at 0° C. to decompose excessive borane-dimethyl sulfide complex. The reaction mixture was then extracted with ethyl acetate and chloroform-methanol (10:1, v/v), and the extract was washed with saturated sodium chloride solution and dried over anhydrous sodium sulfate. The solvent was distilled off under reduced pressure to give the title compound (122.06 g, 86%) as a pale yellow oily product. (This compound was used in the subsequent reaction without further purification.)

$^1$H-NMR (CDCl$_3$) δ: 1.52-1.81 (m, 3H), 2.06 (m, 1H), 3.40-3.85 and 4.04-4.61 (series of m, total 6H), 5.15 (s, 2H, ArCH$_2$), 7.20-7.44 (m, 5H, Ar).

Benzyl (4R)-hydroxy-(2S)-(p-toluenesulfonyloxymethyl)pyrrolidine-1-carboxylate

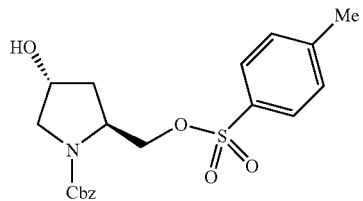

The benzyl (4R)-hydroxy-(2S)-hydroxymethylpyrrolidine-1-carboxylate (120.11 g, 0.478 mol) was dissolved in methylene chloride (1 L), and to this solution were added triethylamine (133.1 ml, 0.956 mol) and 4-dimethylaminopyridine (5.84 g, 47.8 mmol) at 0° C. with stirring. The solution was cooled to −10° C., and p-toluenesulfonyl chloride (100.24 g, 0.526 mol) was gradually added. After completing the addition, the reaction mixture was stirred at the same temperature for 1 hour, and at 5° C. for 18 hours. While cooling this reaction mixture, 1N HCl (500 ml) was added and the solution was extracted with chloroform. The extract was washed with saturated sodium chloride solution and dried over anhydrous sodium sulfate. The solvent was distilled off under reduced pressure to give the title compound as a pale brown oily product. (This compound was used in the subsequent reaction without further purification.)

$^1$H-NMR (CDCl$_3$) δ: 1.80 (s, 1H, OH), 1.99-2.20 (m, 2H), 2.41 and 2.43 (2×s, total 3H, ArMe), 3.32-3.67 (m, 2H), 4.04-4.23 (m, 2H), 4.35-4.53 (m, 2H), 4.88-5.15 (m, 2H), 7.17-7.42 (m, 7H), 7.68 (d, J=8.0 Hz, 1H), 7.74 (d, J=8.0 Hz, 1H).

MS (ESI); m/z: 406 (M$^+$+1).

Ethyl 4-(N-benzyloxycarbonyl-(4R)-hydroxy-(2S)-pyrrolidinylmethoxy)benzoate

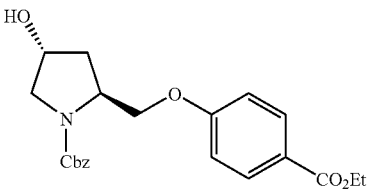

The above benzyl (4R)-hydroxy-(2S)-(p-toluenesulfonyloxymethyl)pyrrolidine-1-carboxylate was dissolved in N,N-dimethylformamide (DMF; 900 ml), and to this solution were added anhydrous potassium carbonate (132.13 g, 0.956 mol) and ethyl 4-hydroxybenzoate (87.37 g, 0.526 mol) at room temperature with stirring. After stirring the reaction mixture at 90° C. for 2 hours, the reaction mixture was cooled, and diluted with ethyl acetate (2000 ml). This diluted solution was washed twice with cooled water and dried over anhydrous sodium sulfate, and the solvent was distilled off under reduced pressure. The resulting residue was purified by column chromatography using silica gel (4 kg), and from the eluate of n-hexane-ethyl acetate (2:1 to 2:3, v/v) was obtained the title compound (76.65 g, 40.1% (the yield of two steps from the benzyl (4R)-hydroxy-(2S)-hydroxymethylpyrrolidine-1-carboxylate)) as a pale orange oily product.

$^1$H-NMR (CDCl$_3$) δ: 1.38 (t, J=7.2 Hz, 3H), 1.66 (brs, 1H), 2.17 (m, 1H), 2.27 (m, 1H), 3.58 (m, 1H), 3.69 and 4.02-4.23 (series of m, total2H), 4.26-4.44 (m, 2H), 4.34 (q, J=7.2 Hz, 2H), 4.58 (m, 1H), 5.05-5.27 (m, 2H), 6.72-6.96 (m, 2H), 7.33 (m, 5H), 7.95 (m, 2H). MS (ESI); m/z: 400 (M$^+$+1)

Ethyl 4-(N-benzyloxycarbonyl-(4S)-hydroxy-(2S)-pyrrolidinylmethoxy)benzoate

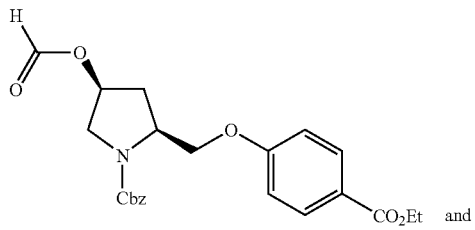

and

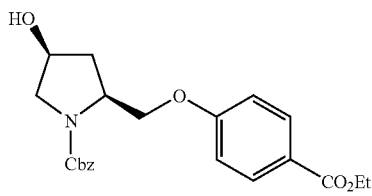

The Ethyl 4-(N-benzyloxycarbonyl-(4R)-hydroxy-(2S)-pyrrolidinylmethoxy)benzoate (76.65 g, 0.192 mol) was dissolved in THF (1.5 L), and formic acid (14.5 ml, 0.384 mol) and triphenylphosphine (55.36 g, 0.211 mol) were added. Diisopropyl azodicarboxylate (41.6 ml, 0.211 mol) was added dropwise to the reaction mixture at 0° C. with stirring. After completing the addition, the reaction mixture was stirred at room temperature for 2.5 hours, and the reaction mixture was exsiccated under reduced pressure. The resulting residue was purified by column chromatography using silica gel (1.0 kg). From the eluate of n-hexane-ethyl acetate (1:1, v/v) was obtained the fraction containing ethyl 4-(N-benzyloxycarbonyl-(4S)-formyloxy-(2S)-pyrrolidinylmethoxy)benzoate. (This fraction contains the impurities from Mitsunobu reaction reagent. This compound was used in the subsequent reaction without further purification.) This fraction was diluted with ethanol (500 ml), and anhydrous potassium carbonate (26.52 g, 0.192 mol) and water (500 ml) were added to the dilution at 0° C. with stirring, and the mixture was stirred at room temperature for 2.5 hours. After concentrating the reaction mixture to half the volume under reduced pressure, the mixture was extracted with chloroform. The extract was dried over anhydrous sodium sulfate, and the solvent was distilled off under reduced pressure. The resulting residue was purified by column chromatography using silica gel (1.5 kg), and from the eluate of n-hexane-ethyl acetate (3:1 to 1:2, v/v) was obtained the title compound (70.50 g, 92.0% (the yield of two steps)) as a pale yellow oily product.

$^1$H-NMR (CDCl$_3$) δ: 1.38 (t, J=7.2 Hz, 3H), 2.13 (m, 1H), 2.36 (m, 1H), 3.24 and 3.54-3.78 (series of m, total 2H), 4.15 (m, 1H), 4.22-4.62 (series of m, Including q at δ4.35, J=7.2 Hz, total 5H), 5.08-5.24 (m, 2H), 6.83 (m, 1H), 6.95 (d, J=8.0 Hz, 1H), 7.34 (m, 5H), 7.92 (m, 1H), 7.99 (d, J=8.0 Hz, 1H). MS (ESI); m/z: 400 (M$^+$+1).

Ethyl 4-(N-benzyloxycarbonyl-(4S)-methoxy-(2S)-pyrrolidinylmethoxy)benzoate

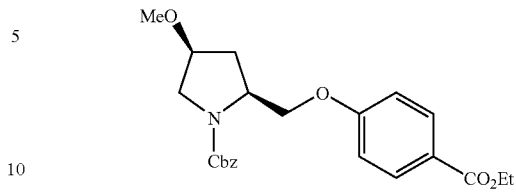

To the ethyl 4-(N-benzyloxycarbonyl-(4S)-hydroxy-(2S)-pyrrolidinylmethoxy)benzoate (70.50 g, 0.176 mol) were added DMF (1.0 L) and methyl iodide (16.5 ml, 0.265 mol), and sodium hydride (60% oil dispersion) (8.47 g, 0.212 mol) was gradually added to the mixture at 0° C. with stirring. The temperature of the reaction mixture was gradually raised to room temperature with stirring, and at room temperature, the mixture was stirred for 3.5 hours. After cooling the reaction mixture again to 0° C., water (1.0 L) and 1N HCl (500 ml) were added, and the mixture was extracted with ethyl acetate (1.0 L×3). The extract was dried over anhydrous sodium sulfate, and the solvent was distilled off under reduced pressure. The resulting residue was purified by column chromatography using silica gel (1.5 kg), and from the eluate of n-hexane-ethyl acetate (2:1, v/v) was obtained the title compound (70.68 g, 96.9%) as a pale orange oily product.

$^1$H-NMR (CDCl$_3$) δ: 1.38 (t, J=7.2 Hz, 3H), 2.07 (m, 1H), 2.32 (brd, J=14.4 Hz, 1H), 3.29 (s, 3H, OMe), 3.51-3.69 (m, 2H), 3.97 (m, 1H), 4.04 (m, 1H), 4.17-4.47 (series of m, including q at δ: 4.34, J=7.2 Hz, total 4H), 5.16 (m, 2H), 6.81 (d, J=8.8 Hz, 1H), 6.97 (d, J=8.8 Hz, 1H), 7.37 (m, 5H), 7.87 (d, J=8.8 Hz, 1H), 7.98 (d, J=8.8 Hz, 1H). MS (ESI); m/z: 414 (M$^+$+1).

Ethyl 4-((4S)-methoxy-(2S)-pyrrolidinylmethoxy)benzoate

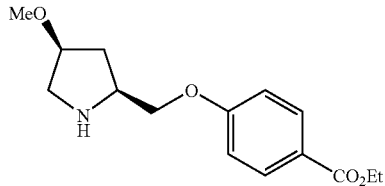

The ethyl 4-(N-benzyloxycarbonyl-(4S)-methoxy-(2S)-pyrrolidinylmethoxy)benzoate (70.68 g, 0.171 mol) was dissolved in ethanol (500 ml), and 10% palladium/carbon (wet, 7.1 g) was added. The mixture was hydrogenated for 18 hours at room temperature with stirring. The reaction mixture was filtered to separate the insoluble content, and the solvent was distilled off under reduced pressure. To the residue were added ethanol (500 ml) and 10% palladium hydroxide/carbon (7.1 g), the mixture was hydrogenated at room temperature for 1.5 hours with stirring. The reaction mixture was filtered to separate the insoluble content, and the solvent was distilled off under reduced pressure to give the title compound (48.47 g) as pale brown oily product. (This compound was used in the subsequent reaction without further purification.)

$^1$H-NMR (CDCl$_3$) δ: 1.37 (t, J=7.2 Hz, 3H), 1.78 (m, 1H), 2.22 (ddd, J=6.4, 7.6, 14.0 Hz, 1H), 3.06 (dd, J=4.8, 12.0 Hz, 1H), 3.22 (dd, J=1.2, 12.0 Hz, 1H), 3.30 (s, 3H, OMe), 3.66 (m, 1H), 3.72 (m, 1H), 3.99 (m, 1H), 4.09 (m, 1H), 4.34 (q, J=7.2 Hz, 2H), 6.92 (m, 2H), 7.97 (m, 2H). MS (ESI); m/z: 280 (M$^+$+1).

Ethyl 4-((4S)-methoxy-(2S)-pyrrolidinylmethoxy)cyclohexanecarboxylate trifluoroacetate

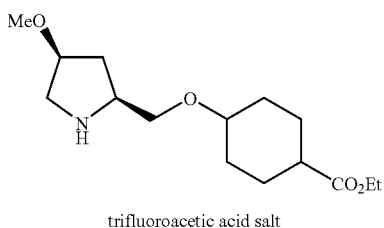

trifluoroacetic acid salt

The ethyl 4-((4S)-methoxy-(2S)-pyrrolidinylmethoxy) benzoate was dissolved in methanol (500 ml) and trifluoroacetic acid (26.3 ml, 0.342 mol), and rhodium-alumina powder (rhodium, 5%) (9.6 g) were added. The mixture was stirred in hydrogen atmosphere (10 to 7.5 MPa) at room temperature for 2 days. The reaction mixture was filtered to separate the insoluble content, and solvent was distilled off under reduced pressure to give the title compound (73.97 g) as a solid product. (This compound was used in the subsequent reaction without further purification.)

$^1$H-NMR (CDCl$_3$) δ: 1.24 and 1.25 (t, J=7.2 Hz, total 3H), 1.36-2.40 (series of m, total 11H), 3.31 (s, 3H), 3.35-3.76 (series of m, total5H), 3.97 (m, 1H), 4.05-4.16 (m, 1H), 4.11 (q, J=7.2 Hz, 2H), 7.95 (br s, 1H, NH), 10.80 (br s, 1H, CF$_3$CO$_2$H).

LC-MS; m/z: 286 (M$^+$+1).

Ethyl 4-(N-tertiary butoxycarbonyl-(4S)-methoxy-(2S)-pyrrolidinylmethoxy)cyclohexanecarboxylate

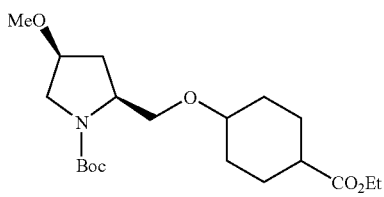

To the ethyl 4-((4S)-methoxy-(2S)-pyrrolidinylmethoxy)cyclohexanecarboxylate trifluoroacetate was added methylene chloride (500 ml), and to this mixture were added triethylamine (47.7 ml, 0.342 mol) and tertiary butyl dicarbonate (41.05 g, 0.188 mol) at 0° C. with stirring. After stirring for 70 minutes, the reaction mixture was exsiccated under reduced pressure, and diluted with ethyl acetate (500 ml). The mixture was washed with 0.5N HCl, and then with saturated sodium chloride solution. After drying over anhydrous sodium sulfate, the solvent was distilled off under reduced pressure. The resulting residue was purified by column chromatography using silica gel (700 g), and from the eluate of n-hexane-ethyl acetate (3:1 to 2:1, v/v) was obtained the title compound (63.68 g, 96.6%, 3 steps) as an oily product.

$^1$H-NMR (CDCl$_3$) δ: 1.24and 1.25 (t, J=7.2Hz, total3H), 1.28-2.38 (series of m, including s at δ: 1.46, total20H), 3.14-4.16 (series of m, including s at δ: 3.30, total 12H). LC-MS; m/z: 286 (M$^+$-Boc+1), 408 (M$^+$+Na).

Ethyl trans-4-(N-tertiary butoxycarbonyl-(4S)-methoxy-(2S)-pyrrolidinylmethoxy)cyclohexanecarboxylate

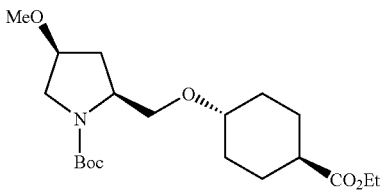

To the ethyl 4-(N-tertiary butoxycarbonyl-(4S)-methoxy-(2S)-pyrrolidinylmethoxy)cyclohexanecarboxylate (63.68 g, 0.165 mol) were added DMF (500 ml) and ethanol (20 ml), and sodium hydride (60% in oil dispersion; 9.91 g, 0.248 mol) was added at 0° C. with stirring. The reaction mixture was stirred at 50° C. for 1 hour, and after cooling again to 0° C., 0.5N HCl (600 ml) was added for acidification. The reaction mixture was extracted with ethyl acetate. The extract was washed with saturated sodium chloride solution, dried over anhydrous sodium sulfate, and the solvent was distilled off under reduced pressure. The resulting residue was dissolved in DMF (300 ml), and anhydrous potassium carbonate (34.21 g, 0.248 mol) and ethyl iodide (6.60 ml, 82.5 mmol) were added with stirring at room temperature. After stirring for 13 hours, the reaction mixture was diluted with ethyl acetate (1000 ml), and washed with cooled water. After drying over anhydrous sodium sulfate, the solvent was distilled off under reduced pressure. The resulting residue was purified by column chromatography using silica gel (150 g), and from the eluate of n-hexane-ethyl acetate (1:1, v/v) was obtained the title compound as a mixture of cis and trans forms. This compound was purified by flash column chromatography (Biotage Flush column chromatography systems), and from the eluate of n-hexane-ethyl acetate (6:1, v/v) was obtained the title compound (27.16 g, 42.7%) as a pale yellow oily product.

$^1$H-NMR (CDCl$_3$) δ: 1.18-1.33 (m, including t at δ: 1.24, J=7.2 Hz, total6H), 1.37-1.53 (m, including s at δ: 1.46, total 11H), 1.91-2.11 (m, 4H), 2.15-2.29 (m, 2H), 3.23 (m, 1H), 3.30 (s, 3H, OMe), 3.32-3.45 (m, 2H), 3.46-4.01 (series of m, total 4H), 4.11 (q, J=7.2 Hz, 2H). MS (ESI); m/z: 286(M$^+$-Boc+1), 386(M$^+$+1).

Ethyl trans-4-((4S)-methoxy-(2S)-pyrrolidinylmethoxy)cyclohexanecarboxyate

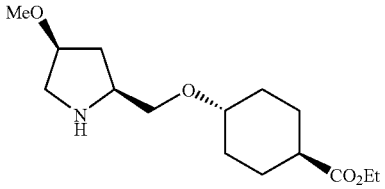

The ethyl trans-4-(N-tertiary butoxycarbonyl-(4S)-methoxy-(2S)-pyrrolidinylmethoxy)cyclohexanecarboxylate (27.16 g, 0.070 mol) was added to 1,4-dioxane (100 ml), and while the solution was stirred at 0° C., 4N HCl/1,4-dioxane (200 ml) was added to the solution. After stirring the reaction mixture at room temperature for another 3 hours, the solvent was distilled off under reduced pressure. The residue was diluted with chloroform (500 ml), and the dilution was neutralized with saturated aqueous solution of sodium bicarbonate and extracted with chloroform-methanol (10:1, v/v) The extract was dried over anhydrous sodium sulfate, and the solvent was distilled off under reduced pressure to give the title compound (22.27 g, crude) as a pale yellow oily product. (This compound was used in the subsequent reaction without further purification.)

$^1$H-NMR (CDCl$_3$) δ: 1.19-1.32 (m, including t at δ: 1.24, J=7.6 Hz, total 5H), 1.38-1.52 (m, 3H), 1.83 (br s, 1H, NH), 1.95-2.13 (m, 5H), 2.25 (m, 1H), 2.87 (dd, J=5.2, 11.6 Hz, 1H), 3.06 (dd, J=1.6, 11.6 Hz, 1H), 3.15-3.32 (m, including s at δ: 3.27, total 5H), 3.45 (dd, J=7.2, 9.2 Hz, 1H), 3.51 (dd, J=4.8, 9.2 Hz, 1H), 3.89 (m, 1H), 4.11 (q, J=7.6 Hz, 2H). MS (ESI); m/z: 286 (M$^+$+1)

Reference Example 2

Ethyl trans-4-((2S,4S)-1-{2,5-dichloro-4-[(1-methylindol-3-yl)carboxamido]phenyl}acetyl-4-methoxypyrrolidin-2-yl)methoxyhexane-1-carboxylate

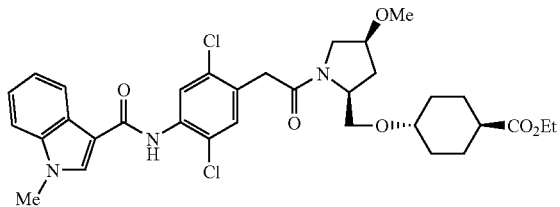

The ethyl trans-4-((4S)-methoxy-(2S)-pyrrolidinylmethoxy)cyclohexanecarboxylate (20.1 g, 70.47 mmol) was dissolved in DMF (400 ml), and 2,5-dichloro-4-[(1-methyl-1H-indol-3-yl)carboxamido]phenylacetic acid (26.58 g, 70.47 mmol), 1-hydroxybenzotriazole(1-HOBt) (1.90 g, 14.09 mmol), 4-dimethylaminopyridine (0.86 g, 7.047 mmol), and 1-ethyl-3-(3-dimethylaminopropyl)carbodiimide hydrochloride (20.26 g, 0.106 mmol) were added to the solution with stirring at room temperature. The reaction mixture was stirred at room temperature for another 18 hours. The reaction mixture was diluted with ethyl acetate (1000 ml), and the diluted solution was washed with 1N HCl. The precipitated insoluble content was separated by filtration under reduced pressure, and was washed with chloroform-methanol (200 ml, 10:1, v/v). After washing the filtrate with a saturated solution of sodium bicarbonate, it was dried over anhydrous sodium sulfate, and the solvent was distilled off under reduced pressure. The resulting residue was purified by column chromatography using silica gel (1.2 kg), and from the eluate of chloroform-ethyl acetate (4:1, v/v) was obtained the title compound (45.35 g, 99.8%) as a pale yellow amorphous product.

$^1$H-NMR (CDCl$_3$) δ: 1.14-1.33 (m, 6H), 1.36-1.55 (m, 2H), 1.92-2.14 (m, 4H), 2.15-2.43 (m, 2H), 3.18-3.35 (m, including 2s, at δ: 3.30, 3.33, total 8H), 3.44-3.58 (m, 2H), 3.62-4.03 (series of m, including s at δ: 3.86, total 8H), 4.09 (q, J=6.8 Hz, 2H), 4.25 (m, 1H), 7.19-7.45 (series of m, total 4H), 7.78 (s, 1H), 8.13 (m, 1H), 8.22 (brd, J=3.2 Hz, 1H), 8.77 (d, J=7.2 Hz, 1H).

MS (ESI); m/z: 644 (M$^+$+1)

Reference Example 3

Trans-4-((2S,4S)-1-{2,5-dichloro-4-[(1-methylindol-3-yl)carboxamido]phenyl}acetyl-4-methoxypyrrolidin-2-yl)methoxyhexane-1-carboxylic acid

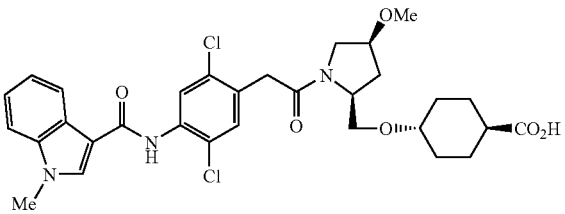

To the ethyl trans-4-((2S,4S)-1-{2,5-dichloro-4-[(1-methylindol-3-yl)carboxamido]phenyl}acetyl-4-methoxypyrrolidin-2-yl)methoxyhexane-1-carboxylate (45.35 g, 70.4 mmol) were added THF (250 ml), methanol (50 ml), and 1N NaOH (250 ml), and the reaction mixture was stirred for 18 hours, and then at 50° C. for 1 hour. The reaction mixture was cooled to 0° C., and 1N HCl was added until the solution became weakly acidic. The mixture was extracted with chloroform-methanol (10:1, v/v), and after drying the extract over anhydrous sodium sulfate, the solvent was distilled off under reduced pressure. The resulting crude crystals were recrystallized from ethyl acetate - methanol (1.5 L, 2:1, v/v) to give the title compound (30.1 g, 69.1%) as fine needle crystals.

IR (ATR) cm$^{-1}$: 2940, 1727, 1598. $^1$H-NMR (DMSO-d$_6$) δ: 1.09-1.43(m, 4H), 1.80-2.22(m, 7H), 3.10-4.30 (series of m, including s at δ: 3.89,total12H), 7.21(dd, J=7.6, 7.6 Hz, 1H),7.28 (dd, J=7.6, 7.6Hz, 1H), 7.49 and7.52 (2S, total 1H), 7.56 (d, J=7.6 Hz, 1H), 7.89 and 7.90 (2S, total 1H), 8.15 (d, J=7.6 Hz, 1H), 8.30 (s, 1H), 9.37 (s, 1H), 12.04 (brs, 1H, CO$_2$H). MS (ESI); m/z: 616(M$^+$+1) Anal; Calcd. for C$_{31}$H$_{35}$Cl$_2$N$_3$O$_6$. 0.75H$_2$O: C, 59.10; H, 5.84; N, 6.67; Cl, 11.25. Found: C, 58.93; H, 5.45; N, 6.70; Cl, 11.64.

Reference Example 4

(4-amino-2,5-dichlorophenyl)acetic acid (20)

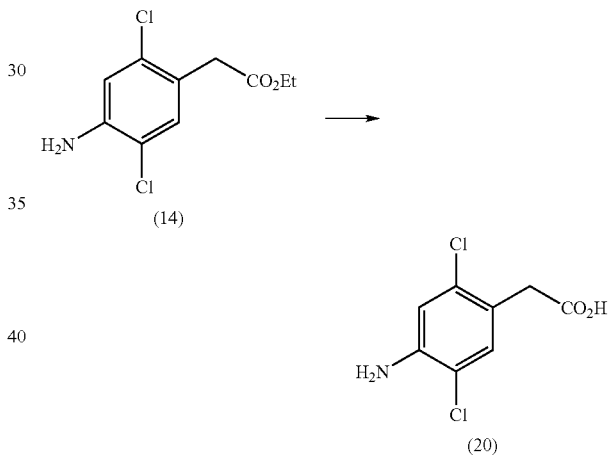

To the ethyl (4-amino-2,5-dichlorophenyl)acetate (14) (4.36 g, 17.57 mmol) were added ethanol (30 ml) and 1N NaOH (35 ml), and the mixture was stirred at room temperature for 1 hour. After adding water (30 ml) to the reaction mixture, the reaction mixture was concentrated to about half the volume under reduced pressure. To this concentrate, 1N HCl (36 ml) was added under cooling, and the precipitated crystals were collected by filtration under reduced pressure. After washing the crystals with water, the crystals were air-dried. The resulting crude crystals were dissolved in ethyl acetate:chloroform:methanol (5:5:2, v/v/v, 120 ml), and the solution was filtered under reduced pressure. The filtrate was concentrated under pressure. The precipitated crystals were washed with hexane, and dried under reduced pressure to give (4-amino-2,5-dichlorophenyl)acetic acid (20) (3.69 g, 96%) as fine prism crystals.

Melting point (uncorrected): 153-163° C. IR (ATR) cm$^{-1}$: 3373, 3249, 1697, 1599. $^1$H-NMR (DMSO-d$_6$) δ: 5.33 (2H, s), 6.86 (1H, s), 7.16 (1H, s). MS (ESI-Nega.) m/z: 218 (M$^+$−1). Anal. Calcd. for C$_8$H$_7$Cl$_2$NO$_2$: C, 43.66; H, 3.21; N, 6.37. Found: C, 43.54; H, 3.21; N, 6.37.

Reference Example 5

Ethyl trans-4-[(2S,4S)-1-(4-amino-2,5-dichlorophenyl)acetyl-4-methoxypyrrolidin-2-yl]methoxycyclohexane-1-carboxylate (21)

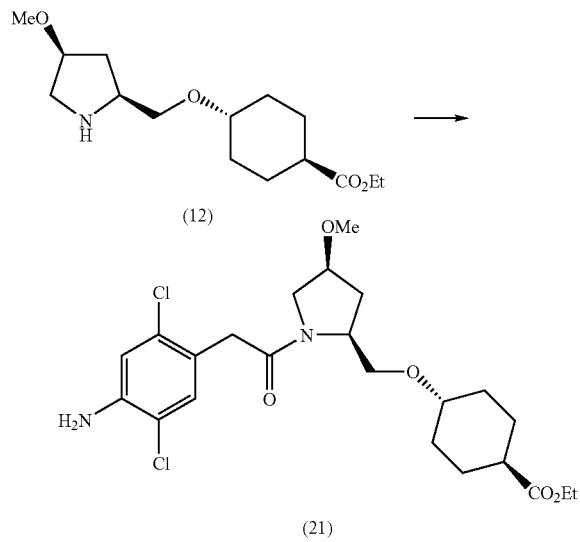

The ethyl trans-4-[(2S,4S)-4-methoxypyrrolidin-2-yl]methoxycyclohexane-1-carboxylate (12) (1.21 g, 5.45 mmol), (4-amino-2,5-dichlorophenyl) acetic acid (20) (1.2 g, 5.45 mmol), 4-dimethylaminopyridine (700 mg, 5.73 mmol), and a catalytic amount of 1-hydroxybenzotriazol were added to DMF (50 ml), and to this mixture was added 1-ethyl-3-(3-dimethylaminopropyl)carbodiimide hydrochloride (1.25 g, 6.54 mmol) with stirring at room temperature, and stirring at room temperature was continued for 15 hours. The reaction mixture was poured into ice water (100 ml), and extracted with ethyl acetate. The extract was washed with saturated sodium chloride solution (twice) and dried over an hydrous sodium sulfate, and the solvent was distilled off under reduced pressure. The resulting residue was purified by column chromatography using silica gel, and from the eluate of chloroform:ethyl acetate (9:1 to 4:1, v/v) was obtained ethyl trans-4-[(2S,4S)-1-(4-amino-2,5-dichlorophenyl)acetyl-4-methoxypyrrolidin-2-yl]methoxycyclohexane-1-carboxylate (21) (2.48 g, 94%) as a colorless solid.

Melting point (uncorrected): 113-118° C. IR (ATR) cm$^{-1}$: 3464, 3303, 3182, 1726, 1633. $^1$H-NMR (CDCl$_3$) δ: 1.22-1.26 (5H, m), 1.42-1.48 (2H, m), 1.95-1.99 (5H, m), 2.03-2.08 (2H, m), 3.22-4.12 (14H, m), 6.78 (1H, m), 7.18 (1H, m). MS (ESI); m/z: 488 (M$^+$-1). Anal.; Calcd. for C$_{23}$H$_{32}$Cl$_2$N$_2$O$_5$: C, 56.88; H, 6.62; N, 5.75. Found: C, 56.57; H, 6.62; N, 5.64.

Reference Example 6

Ethyl trans-4-((2S,4S)-1-{2,5-dichloro-4-[(1-methylindol-3-yl)carboxamido]phenyl}acetyl-4-methoxypyrrolidin-2-yl)methoxycyclohexane-1-carboxylate (13)

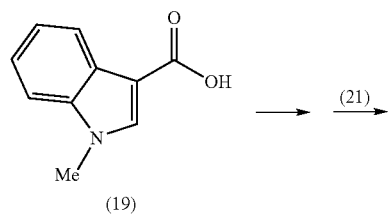

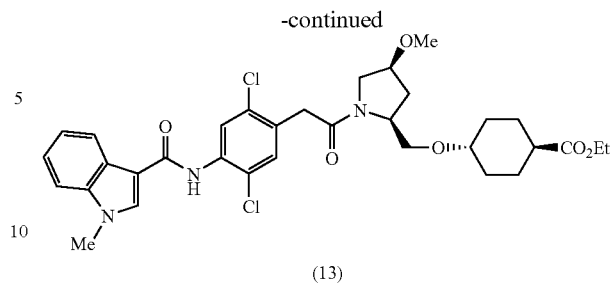

Oxalyl chloride (0.095 ml, 1.07 mmol) was added to 1-methylindol-3-carboxylic acid (19) (150 mg, 0.86 mmol) and 1,2-dichloroethane (3 ml) with cooling in an ice bath and with stirring, and the stirring was continued at the same temperature for 1 hour. The reaction mixture was exsiccated under reduced pressure, and the resulting crystals were dissolved in 1,2-dichloroethane (3 ml). This solution was added to a solution of ethyl trans-4-[(2S,4S)-1-(4-amino-2,5-dichlorophenyl)acetyl-4-methoxypyrrolidin-2-yl]methoxycyclohexane-1-carboxylate (21) (348 mg, 0.714 mmol) in 1,2-dichloroethane (15 ml) at low temperature with stirring. After completing the addition, the reaction mixture was heated under reflux for 10 hours with stirring. After cooling the reaction mixture, it was washed with water and dried over anhydrous sodium sulfate, and the solvent was distilled off under reduced pressure. The resulting residue was purified by column chromatography using silica gel, and from the eluate of chloroform:ethyl acetate (9:1 to 3:1, v/v) was obtained the title compound (350 mg, 76%) as a crystal powder. The spectral data of the compounds obtained by this method were identified with those obtained by the method as described above.

Reference Example 7

Ethyl (2,5-dichloro-4-nitrophenyl)acetate (23)

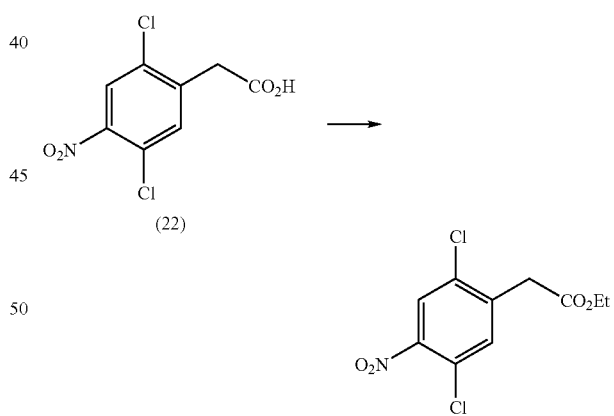

(2,5-dichloro-4-nitrophenyl)acetic acid (22) (Valerie K. Chamberlain and R. L. Wain. Ann. appl. Biol. (1971), 69, 65-72.) (500 mg, 2.0 mmol) was dissolved in ethanol (10 ml), and after adding p-toluenesulfonic acid monohydrate (50 mg, 0.26.mmol), the mixture was stirred at 60° C. for 2 hours. The reaction mixture was cooled to room temperature, and concentrated and exsiccated under reduced pressure. To the resulting residue was added a saturated solution of sodiumbicarbonate (30 ml), and the mixture was extracted with chloroform. The extract was dried over anhydrous sodium sulfate, and the solvent was distilled off under reduced pressure. The resulting residue was purified by column chromatography using silica gel, and from the eluate of chloroform was obtained the title compound (505 mg, 91%) as a pale yellow crystal powder.

Melting point (uncorrected) (washed): 50-55° C. IR (ATR) cm$^{-1}$: 3095, 1716, 1525, 1473, 1365, 1329, 1083. $^1$H-NMR (CDCl$_3$) δ: 1.30 (3H, t), 3.80 (2H, s), 4.21 (2H, m), 7.53 and 7.98 (each 1H, each s). MS (ESI-Nega.) m/z : 278 (M$^+$-1) Anal.; Calcd. for C$_{10}$H$_9$Cl$_2$NO$_4$: C, 43.19; H, 3.26; N, 5.04. Found: C, 42.97; H, 3.15; N, 5.13.

Reference Example 8

Ethyl (4-amino-2,5-dichloro-4-nitrophenyl)acetate (14)

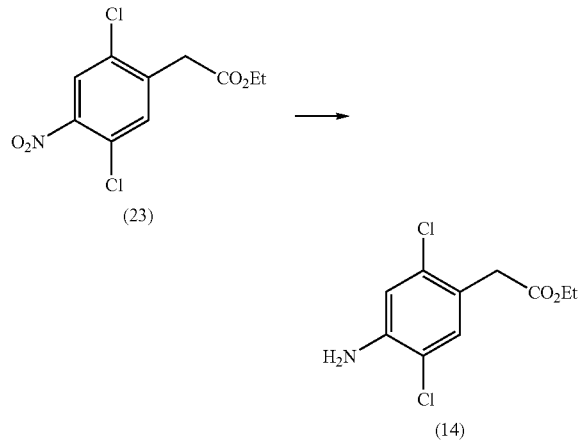

To ethyl (2,5-dichloro-4-nitrophenyl) acetate (23) (400 mg, 1.44 mmol), sodium acetate trihydrate (196 mg, 1.44 mmol) and acetic acid (0.535 ml, 9.35 mmol) were added ethanol (10 ml), water (5 ml), and iron powder (262 mg, 4.67 mmol), and the mixture was stirred at 100° C. for 1 hour. The reaction mixture was cooled to room temperature, and the insoluble content was separated by filtration using celite under reduced pressure. The solvent was distilled off the filtrate under reduced pressure. Ethyl acetate (50 ml) was added to the residue and the mixture was washed with 0.2N HCl, and then, with saturated sodium chloride solution, and dried over anhydrous sodium sulfate. The solvent was then distilled off under reduced pressure, and the resulting residue was purified by column chromatography using silica gel, and from the eluate of chloroform:ethyl acetate (3:1, v/v) was obtained the title compound (278 mg, 78%) as a candy like product.

$^1$H-NMR (CDCl$_3$) δ: 1.26 (3H, t), 3.61 (2H, s), 4.17 (2H, m), 6.79 and 7.16 (each 1H, each d).

The invention claimed is:

1. A process for producing a compound represented by formula (IV) as described below comprising reacting a compound represented by formula (I):

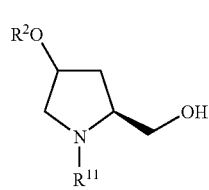

(I)

wherein R$^{11}$ represents a protective group of amino group, and R$^2$ represents hydrogen atom or a protective group of hydroxy group (with the proviso that when both R$^{11}$ and R$^2$ are protective groups, they are not the same protective group) with an optionally substituted arylsulfonyl chloride or an optionally substituted alkylsulfonyl chloride in the presence of a base to produce a compound represented by formula (II):

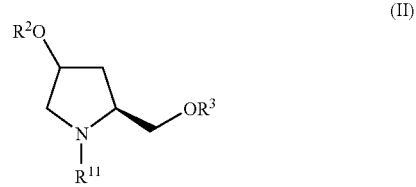

(II)

wherein R$^{11}$ and R$^2$ are as defined above, and R$^3$ represents an optionally substituted arylsulfonyl group or an optionally substituted alkylsulfonyl group; reacting this compound with the compound represented by formula (III):

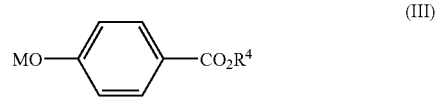

(III)

wherein R$^4$ is an optionally substituted alkyl group or an optionally substituted aralkyl group, and M represents an alkaline metal atom to obtain the compound represented by formula (IV):

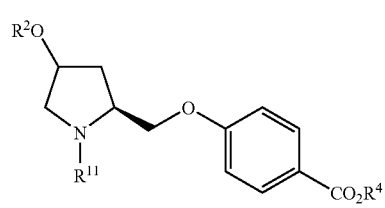

(IV)

wherein R$^{11}$, R$^2$, and R$^4$ are as defined above.

2. The process according to claim 1 wherein R$^{11}$ is benzyloxycarbonyl group.

3. The process according to claim 1 or 2 wherein R$^2$ is hydrogen atom.

4. The process according to claim 1 wherein R$^3$ is para-toluenesulfonyl group or methanesulfonyl group.

5. The process according to claim 1 wherein R$^4$ is methyl group or ethyl group.

6. A process for producing a compound represented by formula (VI-trans) as described below comprising reducing a compound represented by formula (V):

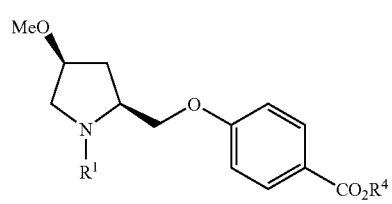

(V)

wherein R$^1$ represents hydrogen atom or a protective group of amino group, and R$^4$ represents an optionally substituted alkyl group or an optionally substituted aralkyl group to produce a compound represented by formula (VI):

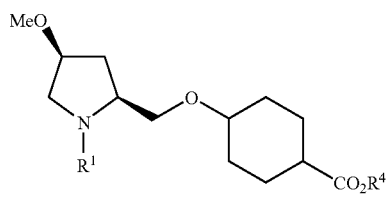

(VI)

wherein $R^1$ and $R^4$ are as defined above; treating this compound with a metal hydride in an aprotic polar solvent; and separating isomers to obtain the compound represented by formula (VI-trans):

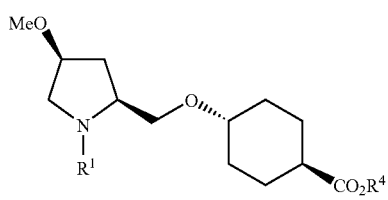

(VI-trans)

wherein $R^1$ and $R^4$ are as defined above.

7. The process according to claim 6 wherein $R^1$ is tertiary butoxycarbonyl group.

8. The process according to claim 6 or 7 wherein $R^4$ is methyl group or ethyl group.

9. The process according to claim 8 wherein the metal hydride is sodium hydride or lithium hydride.

10. The process according to claim 6 wherein the aprotic polar solvent is N,N-dimethylformamide, N-methyl-2-pyrrolidone, or dimethylsulfoxide.

11. A process for producing a compound represented by formula (1):

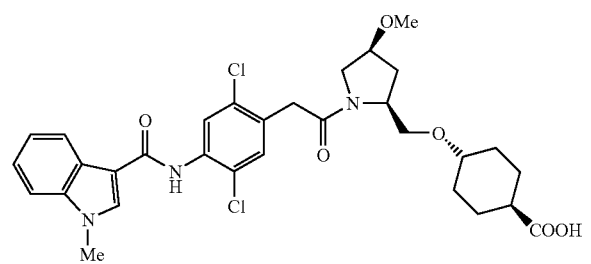

(1)

comprising condensing a compound represented by formula (12):

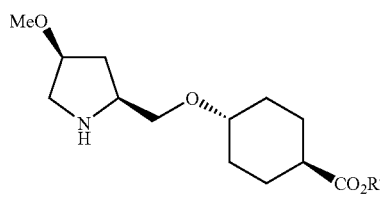

(12)

wherein $R^4$ represents an optionally substituted alkyl group or an optionally substituted aralkyl group with a compound represented by formula (20):

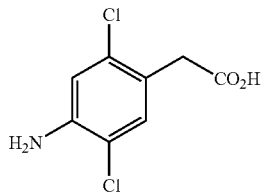

(20)

to produce a compound represented by formula (21):

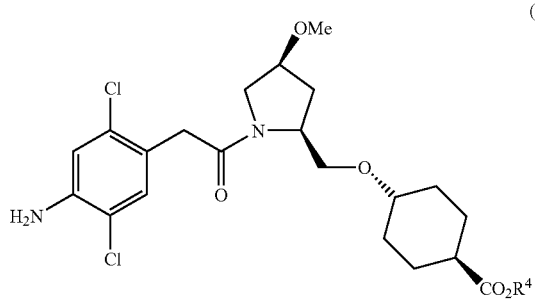

(21)

wherein $R^4$ is as defined above; reacting this compound with a compound represented by the following formula (19):

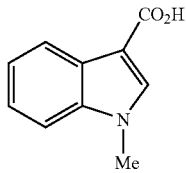

(19)

or its reactive derivative to produce a compound represented by formula (13):

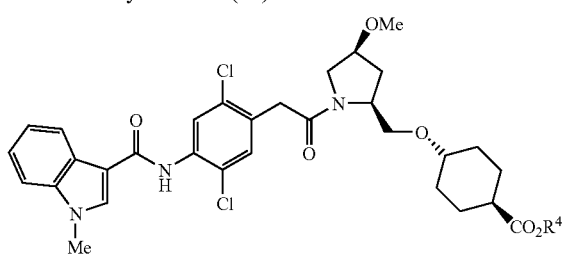

(13)

wherein $R^4$ is as defined above; and cleaving ester group of this compound to produce the compound represented by formula (1).

12. A compound represented by the following formula (21):

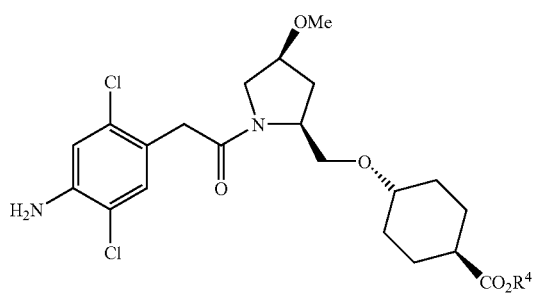

(21)

wherein $R^4$ represents an optionally substituted alkyl group or an optionally substituted aralkyl group.

* * * * *